United States Patent [19]
Riitano

[11] Patent Number: 6,042,375
[45] Date of Patent: Mar. 28, 2000

[54] ENDODONTIC SYSTEMS FOR PROGRESSIVELY, SECTIONALLY AND ANATOMICALLY PREPARING ROOT CANALS WITH SPECIFIC INSTRUMENTS FOR EACH SECTION HAVING PREDETERMINED WORKING LENGTHS

[75] Inventor: Francesco Riitano, Soverato, Italy

[73] Assignee: Ultradent Products, Inc., South Jordan, Utah

[21] Appl. No.: 09/014,762

[22] Filed: Jan. 28, 1998

Related U.S. Application Data

[63] Continuation-in-part of application No. 08/885,906, Jun. 30, 1997, Pat. No. 5,775,904, which is a continuation of application No. 08/656,988, Jun. 6, 1996, Pat. No. 5,642,998.

[51] Int. Cl.[7] ................................................. A61C 5/02
[52] U.S. Cl. ............................................................ 433/102
[58] Field of Search ................................... 433/102, 165, 433/166, 224

[56] References Cited

U.S. PATENT DOCUMENTS

| | | |
|---|---|---|
| 322,265 | 7/1885 | Donaldson . |
| 621,873 | 3/1899 | Vajna . |
| 1,168,052 | 1/1916 | Bolls . |
| 1,369,112 | 2/1921 | Jones . |
| 4,231,738 | 11/1980 | Riitano et al. ................ 433/102 |
| 4,332,561 | 6/1982 | McSpadden .................... 433/102 |
| 4,353,696 | 10/1982 | Bridges ........................ 433/125 |
| 4,364,730 | 12/1982 | Axelsson ...................... 433/141 |
| 4,518,356 | 5/1985 | Green .......................... 433/102 |
| 4,571,183 | 2/1986 | Nash ........................... 433/116 |
| 4,836,780 | 6/1989 | Buchanan ...................... 433/102 |
| 4,850,867 | 7/1989 | Senia et al. ................... 433/102 |
| 4,889,487 | 12/1989 | Lovaas ......................... 433/102 |
| 4,971,556 | 11/1990 | Riitano ........................ 433/102 |
| 4,992,048 | 2/1991 | Goof ........................... 433/102 |
| 5,017,138 | 5/1991 | Schilder ....................... 433/102 |
| 5,026,284 | 6/1991 | Martin ......................... 433/102 |
| 5,219,284 | 6/1993 | Velvart et al. ................. 433/102 |
| 5,257,934 | 11/1993 | Cossellu ....................... 433/102 |
| 5,498,158 | 3/1996 | Wong .......................... 433/102 |
| 5,503,554 | 4/1996 | Schoeffel ...................... 433/102 |
| 5,605,460 | 2/1997 | Heath et al. ................. 433/102 X |
| 5,642,998 | 7/1997 | Riitano ........................ 433/224 |
| 5,658,145 | 8/1997 | Maillefer et al. ............... 433/102 |
| 5,735,690 | 4/1998 | Malentacca .................... 433/102 |
| 5,752,825 | 5/1998 | Buchanan .................... 433/102 X |

FOREIGN PATENT DOCUMENTS

| | | |
|---|---|---|
| 136500 | 4/1984 | European Pat. Off. . |
| 2373269 | 4/1984 | France . |
| 2597327 | 4/1986 | France ................................ 02/5 |
| 1169326 | 7/1983 | Italy . |
| 1199941 | 3/1985 | Italy . |
| 2022475 | 1/1979 | United Kingdom . |

Primary Examiner—Nicholas D. Lucchesi
Attorney, Agent, or Firm—Workman, Nydegger & Seeley

[57] ABSTRACT

A root canal is sequentially cleaned in sections from the crown to the apex. An opening is first formed into the tooth to provide access into the root canal. The opening is preferably rectified to remove obstructions from fully accessing the anatomical root canal. The pulp material is then sequentially removed from the portion of the root canal above the apical portion of the root canal with a first set of instruments and then from the apical portion with a second set of instruments. Cleaning of the pulp material from the root canal also shapes the root canal to ease filling of the root canal with a filling material. Each instrument comprises a handle connected to a file. Each file has an abrading portion and terminates at a tip. The files used to clean the portion of the root canal above the apical portion have properties which enable the abrading portion of the file to conform to the configuration of the root canal while simultaneously moving the file in a cleaning motion.

49 Claims, 27 Drawing Sheets

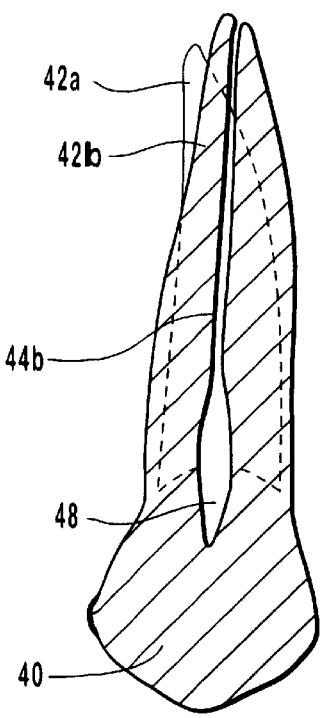 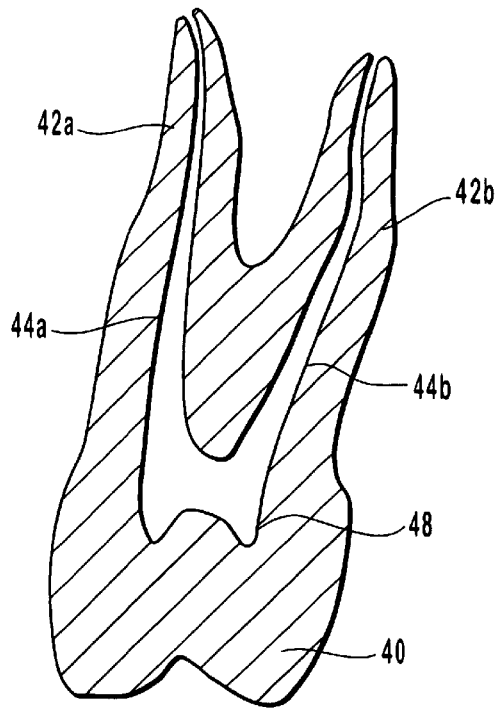
FIG. 4A    FIG. 4B
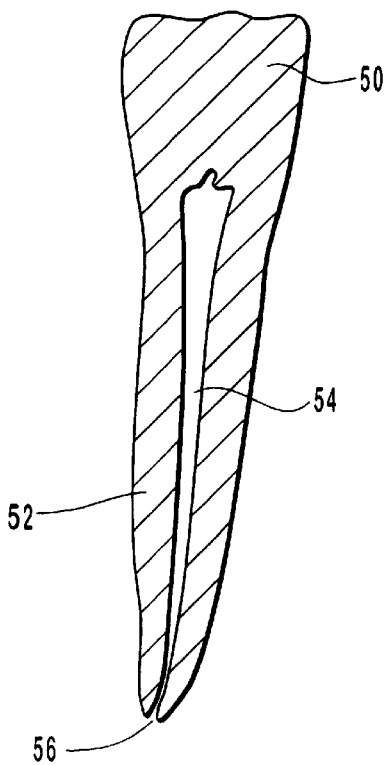 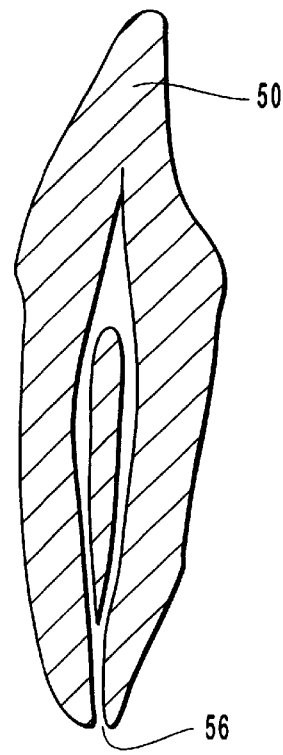
FIG. 5A    FIG. 5B

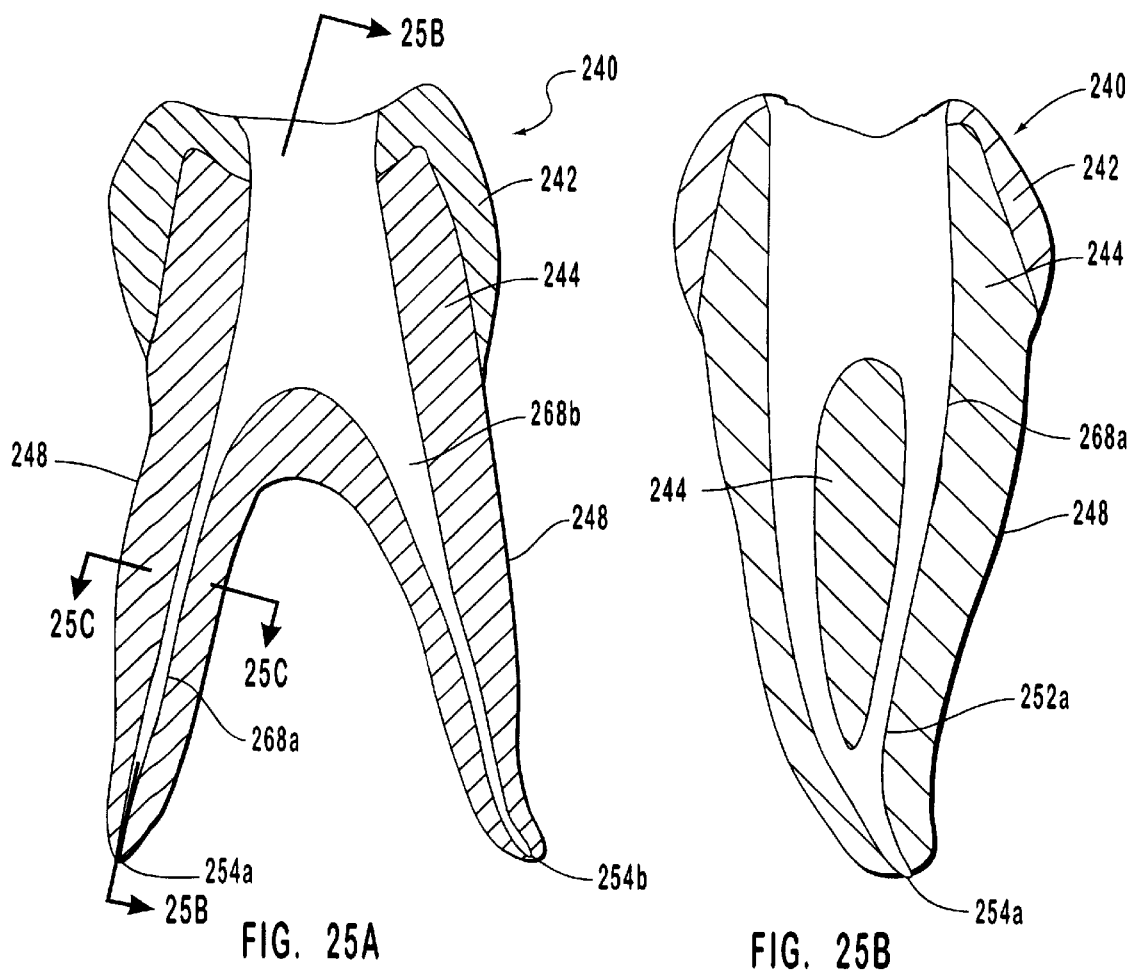
FIG. 25A
FIG. 25B
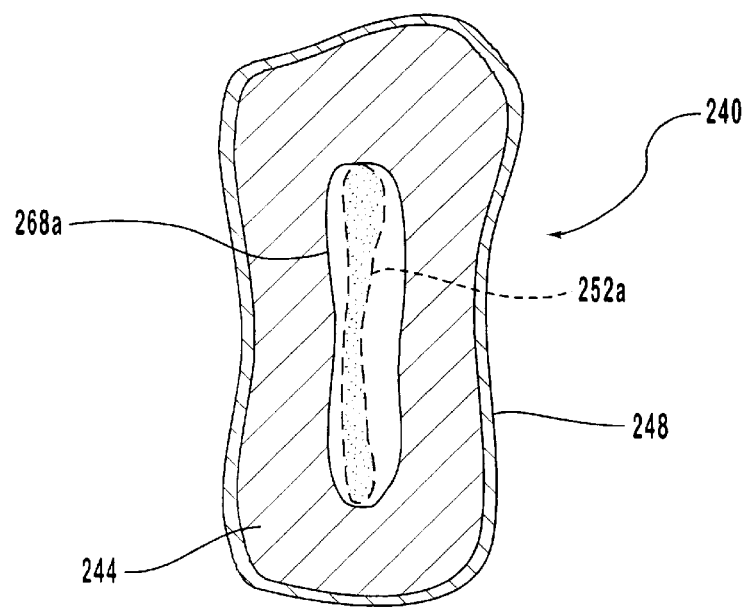
FIG. 25C

ENDODONTIC SYSTEMS FOR PROGRESSIVELY, SECTIONALLY AND ANATOMICALLY PREPARING ROOT CANALS WITH SPECIFIC INSTRUMENTS FOR EACH SECTION HAVING PREDETERMINED WORKING LENGTHS

RELATED APPLICATIONS

This application is a continuation-in-part of U.S. patent application Ser. No. 08/885,906 filed on Jun. 30, 1997, now U.S. Pat. No. 5,775,904 which is a continuation of U.S. patent application Ser. No. 08/656,988, filed Jun. 6, 1996, which issued on Jul. 1, 1997 as U.S. Pat. No. 5,642,998. Priority of U.S. Pat. No. 5,642,998 is based on Italian Patent Application No. RM95A000377 which was filed on Jun. 6, 1995. For purposes of disclosure of the present invention, each of the foregoing applications is incorporated herein by specific reference.

BACKGROUND OF THE INVENTION

The Field of the Invention

The present invention is related to the field of endodontistry. More particularly, the invention is related to the systems and methods for treating root canals.

The Relevant Technology

To preserve a tooth with a pulp that is diseased or is potentially diseased, it is generally necessary to remove the pulp material in the pulp canal from the tooth, to shape the root canal(s), to prevent or minimize the presence of bacteria through the use of irrigants and dressings, to clean the walls of the root canal(s), to eliminate the smear layer made during instrumentation of the root canal(s) to open the dentinal tubules. These steps are all done to prepare the root cavity for being filled or obturated with biocompatible materials, such as gutta percha, before the pulp cavity is sealed, thereby promoting the healing and functional recovery of the tooth. This procedure is referred to as root canal therapy.

Root canal preparation, which generally involves the pulp removal and cleaning of the root canal walls as well as shaping of the canal walls, is typically achieved by mechanical or hand instrumentation with files or bits that are configured to bore and/or cut. Mechanical instrumentation can be achieved through the use of endodontic handpieces that give instruments such as files a rotational motion, reciprocal motion, sonic movements or ultrasonic movements.

Before endodontic therapy is begun, a preoperative x-ray is prepared to assess the health and the pathological status of the tooth and to determine the approximate length of the the root canal in order to select an instrument for use in root canal with an appropriate working length. The x-ray yields an image, such as the schematic representations shown in FIGS. 1A and 1B, which generally show teeth 10 with sufficient clarity to view some of the properties of roots 12 and the root canals 14 located therein, particularly the location of the radiographic apex 17 just beyond the apical foramen 16. The distance between radiographic apex 17 and a fixed reference position on the occlusal surface of a tooth is used to determine the working length of the instrument. FIG. 1B, an enlarged view of root 12a shown in FIG. 1A, shows the relative position of the radiographic apex designated at line 17 with that of the endodontic apex and the anatomical apex designated respectively by lines 18 and 19.

Preoperative or intraoperative x-ray images of a tooth requiring endodontic treatment, such as the x-ray image depicted in FIG. 1A, are obtained by lingual placement of film packets as shown in FIG. 2 at 22 and by a x-ray film packet holder (not shown) and a long cone x-ray head (not shown) seated outside of the cheek. Although, x-ray images formed as shown in FIG. 2 from a buccal-lingual x-ray projection are generally useful for determining the length of the root canal and the working length for a file, such images provide only limited information regarding the overall anatomy of the root canal and can also be misleading as to the actual length of the root canal.

The information is limited because only one dimension of the overall anatomy of the pulp cavity can be viewed in vivo. Such images show only a linear aspect of the root canal but cannot show a tridimensional view of a tooth and its root canal(s). Although, it would be very helpful to view a tooth from a position between the teeth or from the interproximal space such a mesial-distal view cannot be clearly produced when the tooth is still positioned in a patient's mouth.

The difficulties presented to an endodontist in assessing the overall anatomy of teeth from just the x-ray images obtained from buccal-lingual x-ray projections can be clearly identified with reference to FIGS. 3–6. FIGS. 3A–6A are longitudinal cross-sectional schematic views of extracted teeth taken from the front or back of the respective tooth which corresponds with the images obtained from buccal-lingual x-ray projections. FIGS. 3B–6B depict longitudinal cross-sectional schematic views of the same extracted teeth shown in FIGS. 3A–6A from the mesial-distal or side view that cannot be obtained or seen while the teeth are still positioned in a patient's mouth.

FIGS. 3–4 illustrate the necessity for practioners to rely heavily on their experience and knowledge of typical anatomical structures to properly prepare a root canal. FIG. 3A depicts a lower premolar 30 from the buccal-lingual view of the tooth which shows root 32 and a root canal 34 therein that appears to be rather narrow and to have a relatively uniform perimeter along its length. FIG. 3B, however, shows that when seen from the mesial-distal view, the root canal is initially wide and then tapers significantly before reaching the apical foramen 36. The practioner may not be able to accurately assess the anatomical structure of the root anatomy when limited to knowledge derived from an x-ray corresponding to the image shown in FIG. 3A. Similarly, FIG. 4B, which depicts an upper premolar 40 with roots 42a and 42b and root canals 44a and 44b located therein, illustrates the need for practioners to rely merely on accumulated experience and knowledge of typical anatomical structures as the configuration of pulp chamber 48 may be difficult to accurately ascertains from only a x-ray photograph that corresponds with the image shown in FIG. 4A.

Additionally, practioners encounter anatomies with widely varying aberrations and intercommunications of root canals. FIG. 5A depicts a mandibular or lower incisor 50 from the buccal-lingual view of the tooth which shows root 52 and root canal 54. FIG. 5B depicts the same lower incisor 50 from the mesial-distal view of the tooth. The mesial-distal view shown in FIG. 5B clearly shows that root canal 54 branches and then merges to have a single foramen 56. This common root canal morphological variation shown in FIG. 5B may not be ascertainable to a practioner as the practioner can only obtain a preoperative or intraoperative x-ray image of lower incisor 50 which corresponds to FIG. 5A. Similarly, a root canal may branch without merging to yield multiple foramina as shown in FIGS. 6A–6B which depict a lower first molar 60. Again, the buccal-lingual view, as shown in FIG. 6A, provides inadequate information compared with the depiction taken from the mesial-distal view of mesial root 62b in FIG. 6B wherein branches 64a and 64b are shown which do not merge and accordingly have two foramina 66a and 66b.

In addition to the morphological variations in anatomy as discussed above, there are also substantially different perimetrical configurations of root canals. The shape of root canal perimeters varies not only between different types of teeth but also along the length of a single root canal of a tooth as is illustrated in FIGS. 7A–7B.

FIG. 7A depicts a maxillary right first molar 70 with cutting lines which show the division of the tooth into transverse cross-sections for segmentation as shown in FIG. 7B. FIG. 7B displays roots, 72a, 72b and 72c, of molar 70 cut into four respective segments, 80–83, to clearly show the variations of root canals 74a, 74b and 74c. Also displayed in FIG. 7B are segments 84 and 85 which respectively contain the floor of the pulp chamber 78 and pulp chamber 78. Contrasting the perimeters of root canals 74a, 74b and 74c beginning in segment 84 as each root canal tapers to its respective apices 76a, 76b and 76c clearly shows that the perimeter anatomy varies along the length of each root canal.

As indicated above, root canals have a variety of perimetrical or circumferential anatomies depending on the type of tooth. Accordingly, the practioner must utilize instruments in root canals with diverse perimetrical anatomies that each also vary and transition in the configuration of their respective perimeters along their root canal lengths. FIG. 8 shows cross-sectional views of different teeth 90a–90l that have been extracted and then cut along a transverse cross-section of the tooth to show root canals 92a–92l as well as corresponding pulp chambers 94 and floors or cervical aspects 96. File instruments 98 are also shown inserted into root canals 92. From this view, which can only be seen in vitro, it is evident that a high degree of variation occurs in the perimetrical anatomy of the pulp cavity of teeth.

FIG. 9 shows the general division of root canal perimetrical anatomies into those that have primarily a tubular morphology and those that have primarily a laminar morphology. The tubular perimetrical anatomies include root canals such as those shown at 100, 101, and 102 which are respectively primarily oval, round and triangular. The laminar perimetrical anatomies include root canals with essentially slit-like configurations such as those shown at 103, 104, and 105 which are respectively primarily straight, semilunar shaped and figure eight shaped.

From the discussion above, it is apparent that when a practitioner views a preoperative or interoperative x-ray image of a tooth the practitioner can only guess about the actual anatomy of the pulp cavity and the root canal system. While the practitioner may be able to confirm that a root canal has been cleaned along the length of the pulp chamber from the coronal portion to the apex of the root, the length that has been contacted or abraded by the file may only be a portion of the root canal system.

However, without a correct understanding of the overall root canal anatomy due to the inability to see the root canal from the mesial-distal view or the perimetrical anatomy on different points along the length of the root canal, the practioner can never value the relationship between the instrument inserted in the root canal with the canal walls. Accordingly, as shown in FIG. 10, when a root canal 112a–c of a tooth 110a–c is cleaned by merely inserting a file instrument 114 into each tooth 112a–c and then rotating the instrument, significant portions are not cleaned. The inability to clean all surfaces of a root canal by merely inserting a file instrument is further illustrated in FIG. 8 wherein the position of file instrument 98 is shown in transverse cross-sectional views of root canals. FIG. 8 shows that boring from one position into the root canal will often miss large sections of the perimeter of the root canal, thereby leaving portions of diseased or necrotic pulp material undisturbed which can ultimately cause undue pain, lengthy healing times or even cause the procedure to fail. One of the reasons sodium hypochlorite is used is to compensate for the failure to adequately clean the entire perimeter.

The inability to fully identify the anatomy of the pulp cavity restricts the ability of the practitioner to confidently conclude that the procedure has been successful. However, many dentists are not overly concerned with completely cleaning the entire root canal since their failure rate is not at an unsatisfactory level.

To compensate for the inability to contact all root canal surfaces and the lack of knowledge of the actual anatomy of the root canal, conventional cleaning techniques involve sequential increases in the diameter of instruments inserted into the root canal. The primary conventional systems and methods for removing pulp material from the root canal of a tooth are the step-back technique and the crown-down technique. The step-back technique involves cleaning the root canal from the apex to the crown while the crown-down technique involves cleaning the root canal from the crown down to the apex. Each has its own unique benefits and disadvantages.

The step-back technique involves the use of a set of file instruments which are sequentially inserted into a root canal after the root canal has been exposed by removing the roof of the pulp chamber as shown in FIG. 11A and FIG. 11B with an instrument 120 with bur 122. After the overhanging portions of enamel 152 and dentin 154 have been removed to provide access into the pulp chamber, pulp material 160 can be removed. FIG. 12 depicts a set of step-back file instruments with each file instrument 130 comprising a handle 132 connected to a file 134 or a shaft with tines or an abrading portion. Each file has a tip 136 opposite atop end 138 where file 134 joins handle 132. As viewed in FIG. 12 from left to right, the diameter at top end 138 of each file increases progressively from the smallest to the largest such that the diameter of 138a is less than the diameter of 138b. The diameter of each successive file at tip end 136 is also successively larger. Accordingly, the taper of each file remains essentially the same even though each file is progressively larger that the preceding file.

In the step-back technique, the apical portion of the tooth is prepared first and then the canal is flared from apex to crown. The process essentially involves inserting a series of progressively larger files to the apex of the root canal and rotating each file and/or moving the file up and down in a longitudinal motion until a file can be entered that is considered a standard size for completing the process or that meets some resistance to rotation. The rest of the canal is then flared by sequentially using each file in the set as shown in FIG. 12 with each file being larger than the preceding file and by alternately advancing and then withdrawing each instrument.

FIG. 13A depicts molar 150 being prepared by the step-back technique after the enamel 152 and dentin 154 have been removed that overhang pulp chamber 156 and after the first step of the step-back technique has been achieved by inserting a file into pulp chamber 156 and into root canal 158a to remove material 160 in the lower portion of the canal above the apex or apical end 162a. After the portion above apex 162a is cleaned, each file shown in FIG. 12 is sequentially inserted down to apical end 162a of root canal 158a beginning as shown in FIG. 13A with file instrument 130a. As a result of this technique, the diameter of the area being contacted at the apical portion is increasingly larger.

FIG. 13B is a cross-sectional view taken along cutting line 13B—13B in FIG. 13A of tooth 150 during cleaning of root canal 158a with file instrument 130a in the step-back technique. Insertion of the files of the other file instruments 130b and 130c will further clean material 160 as the diameter of each file is increasingly larger, however, the files are also increasingly rigid. As the rigidity increases, the flexibility of the files decreases and as result it becomes increasingly difficult for the files to adjust to the contours of the surfaces of the root canal to clean all of the surfaces of the root canal and increases the likelihood that the files will remove too much of the surrounding dentin 154.

The views depicted in FIGS. 13A and 13B depict the problem previously discussed with regard to the difficulty in assessing the actual root canal anatomy in vivo. When viewed in FIG. 13A, it appears that the root canal has been cleaned, however, FIG. 13B shows that a significant portion of material 160 remains. Accordingly, when the root canal is viewed in an x-ray photograph which is the same view shown in FIG. 13A, a practitioner may mistakenly believe that the tooth has been adequately cleaned. This mistaken belief may be further incorrectly relied on as the root canal is widened by the insertion of the larger files and the large files cannot be used to properly follow the contours of the root canal to fully clean the root canal. Accordingly, there is some possibility for failure of the root canal therapy.

Additionally, since each file is more rigid than the preceding file, the ability to safely move the file within the canal is limited. Further, the increasing rigidity results in decreased ability to negotiate the curves in the canal and to clean all of the surfaces or walls of the canal. A significant problem that can result from inserting increasingly rigid files and also from initially inserting a file all the way down to the apex is apical perforation. As shown in FIG. 14A, after tooth 170 has been prepared by removal of portions of the enamel 172 and dentin 174, file 132 has been inserted into root canal 176 and perforated apex 178. Perforating the apex can also result from an error in estimating the length of a root canal, by failure of a stop such as stop 140 to remain at a predetermined position or by failure to observe the hatch markings on the file which can be used instead of a stop to designate the length.

The apex can be perforated by extrusion of the infected material 180 through the apex due to the force exerted by the file on the material as the file is pushed downward to reach the apex. The potential for extruding infected material through the apical foramen of a necrotic tooth by initially inserting a file instrument all the way down to the apex is a particular disadvantage of the step-back technique. More particularly, it is a disadvantage that the procedure has identical steps for working in either necrotic or vital root canals. In addition to exposing the tissue surrounding the tooth to the infected material, apical perforations may allow irrigants and filling or obturating material to flow out of the apex. Such apical perforations, as well as wall perforations, may delay tooth healing and may compromise the outcome of the therapy.

Perforations can also occur due to a failure to maintain a proper working length of the instrument during the procedure. As the canal is widened, curvatures are straightened which decreases the length needed for the instrument to work. Accordingly, the rubber stop 140 must be adjusted. To properly determine the appropriate working length, many radiographs are necessary throughout the operation as the canal is modified. The time required to obtain the x-ray photographs or images and to adjust the working length of the instruments results in a lengthy process. The step-back technique is also time intensive as a large number of instruments are required to complete the root canal therapy.

As shown in FIG. 14B, another problem is the formation of ledges such as ledge 182. Ledges can occur when a practitioner attempts to insert a file such as file 134 to the apex and the file is too inflexible to properly curve with the root canal or move around a protrusion. When a file is too inflexible to flex as needed and prematurely comes to a stop, the downward pressure exerted on the file causes the file to dig into the side of the root canal and form a ledge. Such ledges are difficult to bypass and if the ledge occurs very close to the apex, the ledge may give the practitioner the mistaken impression that the apex has been reached.

The crown-down technique was developed partially to decrease the amount of instrumentation required to clean a root canal by the step-back technique. However, the crown-down technique does not avoid the problems set forth above in relation to the potential for perforation and ledging.

The crown-down technique generally involves the use of a set of file instruments wherein each file in the set of file instruments has a different diameter at the top of the file where the file joins the handle. The diameter at the top of each file is progressively larger than the preceding file. As a result of this configuration, the taper of each file is larger than the preceding file in the set. By using such files, the area being abraded, particularly in the anatomical coronal portion, is abraded with files of increasingly larger diameters.

Based on the greater flexibility of files formed from nickel/titanium compared with files formed from steel, proponents of nickel/titanium files have asserted that such nickel/titanium files are more likely to follow root canal curvatures and to stay in the center of the root canal, thereby decreasing the likelihood of ledging or perforating the root canal walls. As set forth hereinbelow in greater detail, each material has its own unique advantages and disadvantages.

The ability of a nickel/titanium file to stay in the center is not necessarily desirable. By remaining in the center, the file instrument works contemporaneously and indiscriminately on all walls within reach of the file. Since root canal walls do not have equal thicknesses in all direction and at all different points along a root canal, some walls can be overthinned or perforated. Additionally, nickel/titanium file instruments can be too flexible to adequately clean the root canal as the file may bend and be deformed when it encounters a hard substance. Since the nickel/titanium files are flexible, they tend to follow the path of least resistance and cannot be used to aggressively clean the portions that are difficult to reach. Accordingly, when a nickel/titanium file is used to clean a non-cylindrically shaped root canal, the file moves only at the center of the canal and/or the area of least resistance and fails to remove all of the necrotic tissue.

FIGS. 15A, 15B, 15C, 15D and 15E depict transverse cross-sections of a tooth 190 that has been cleaned in a manner that has resulted in either overthinning of root canal walls, perforation of a root canal wall or excessively weakening of a tooth. These problems result primarily from the use of files with increasingly larger tapers and increasing rigidity in accordance with the crown-down technique which prevents the files from being laterally moved to enable the file to clean the entire perimeter of the root canal. The cross-sections shown in FIGS. 15A–E may be considered independently from each other as being cross-sections from different teeth or from a single tooth such that FIG. 15A shows two roots 192a and 192b of a tooth 190 while FIGS. 15B–15E show root canal 194a as the root canal tapers to the apex.

FIG. 15A depicts the overthinning that can occur to the furcation walls of root canals 194a and 194b as a result from the indiscriminate thinning of root canal walls by maintaining a file instrument in a central location. Such overthinning and potential furcal perforation can have devastating results. The inability to adequately direct a file used in accordance with the crown-down technique based on the practioner's knowledge of the relative thicknesses of the portions of canal walls is a significant disadvantage of the technique.

In FIG. 15B, a lateral perforation has occurred as a hole has been formed through dentin 198 and cementum 197 during the cleaning of root canal 194a. As in FIG. 15B, the resulting from the formation of borehole 196a may be obscured from the x-ray. The practitioner may then mistakenly conclude that the root canal has been successfully cleaned without realizing that there is a perforation.

In FIG. 15C, root canal 194a has been overly thinned as borehole 196a extended through dentin 198 and into the cementum 197 during the cleaning of root canal 194a. The excessive thinning resulting from the formation of borehole 196a may be obscured from the x-ray view due to concavities or curvatures in the root canal. As a result, the practitioner may not realize that the borehole extends into the cementum and may therefore mistakenly conclude that the root canal treatment has been successful. Infective bacteria that remained in the root canal, perhaps in the portions that were not contacted with the files, as well as toxins produced by the bacteria may then permeate through the cementum and cause infection or other complications.

Root canal therapy resulting in the configuration shown in FIG. 15D may be successful even though only a portion of root canal 194a has been cleaned as evidenced by borehole 196a. It would, however, be preferable to be able to remove and clean essentially all pulp material by cleaning the entire perimeter. Although, it would be preferred to clean the root canal without missing significant portions, the configuration shown in FIG. 15D is the standard result of the crown-down technique. As with the step-back technique shown in progress in FIGS. 13A and 13B, the x-ray view of tooth 190 would give the impression that the root canal had been cleaned. Additionally, the use of a set of files with increasing tapers would further contribute to a potentially incorrect conclusion that cleaning by such a conventional process had resulted in removing all material from root canal 194a.

As in the configuration shown in FIG. 15D, the configuration shown in FIG. 15E may also result in successful root canal therapy. Although, borehole 196a does not extend through dentin 198 and into the cementum 197, the borehole 196a is significantly larger than root canal 194a was as shown by the phantom lines. The excessive thinning may resultingly significantly weaken tooth 190.

The configuration of the large borehole 196a as shown best in FIGS. 15B, 15C, 15D and 15E results primarily due to the shape and properties of the files. The use of files with increasingly larger tapers limits the range of motion of the files. Due to the use of files with successively larger tapers which therefore are increasingly rigid, each file is primarily limited to being rotated without substantial lateral movement such that the tip of each file acts as a rotation point and remains in essentially the same location as the file is rotated. Each successive file can move less laterally and makes a bigger borehole than the preceding file. Accordingly, the files cannot clean a root canal without significantly altering the original anatomy by leaving a footprint or borehole corresponding to the configuration of the instruments used. More specifically, the result is a footprint or borehole with a perimeter that corresponds to the perimeter of the biggest file that extends well beyond the original anatomy of the root canal and yet in most instances does not adequately clean significant portions of the root canal.

The configuration of borehole 196a, which substantially deviates from the original anatomy of the root canal 194a, is due also to the flexibility of the files used in the crown-down technique which are typically formed from nickel/titanium. The flexibility of the files prevents the files from being successfully urged against the perimeter or against the various surface features of the root canal. The flexibility of the files also increases the tendency of the files to remain in the center or at the location where less resistance to movement is encountered.

There are also other disadvantages to the use of nickel/titanium files. Nickel embodied in the alloy may potentially result in an allergic reaction. Nickel/titanium files are brittler and softer than stainless steel. Accordingly, nickel/titanium files may break more easily and suddenly than steel. When a nickel/titanium file instrument is used with a large file diameter the flexibility decreases to the point of being as rigid as stainless steel and yet it can break more easily. Additionally, nickel/titanium files costs about four times as much as steel files and yet nickel/titanium files generally wear out faster than steel files. Nickel/titanium files wear out so quickly that some manufacturers mark their products as being intended for single use only.

Although, the crown-down technique typically enables a practitioner to more efficiently clean a root canal than the step-back technique, they both require the practitioner to utilize many different instruments. The need to frequently change the cleaning instrument results in significant time requirements for cleaning a root canal. However, careful instrumentation in accordance with either tedious time consuming method does not avoid the problems set forth above in relation to apical perforation, wall perforation, overthinning or failure to clean all of the wall surfaces.

Based on the foregoing, methods and systems are needed in the endodontic arts which enable a dental practitioner to remove and clean essentially all pulp material in a root canal requiring root canal therapy.

It would also be an advancement in the endodontic arts to provide methods and systems that enable a practitioner to remove and clean pulp material in a root canal in a safer manner than conventional techniques and which does not substantially alter the anatomy of the root canal.

Additionally, it would be an advancement in the endodontic arts to provide methods and systems that enable a practitioner to remove and clean pulp material in a root canal in a manner that is at least as efficient as conventional techniques and is less likely to result in failure due to overly thinning the root canal, perforations or due to infected material being pushed beyond the root from the coronal aspects of canals.

SUMMARY AND OBJECTS OF THE INVENTION

An object of the present invention is to provide, methods and systems which enable a dental practitioner to remove and clean essentially all pulp material in a root canal requiring root canal therapy by progressive sections of the root canal from the crown to the apex.

Another object of the present invention is to provide methods and systems such that pulp material in a root canal can be cleaned and removed in a safe manner without substantially altering the anatomy of the root canal.

Additionally, another object of the present invention is to provide methods and systems that enable a practitioner to efficiently remove and clean pulp material in a root canal by progressive sections in a manner that is less likely to result in failure due to overly thinning the root canal, perforations, etc. than conventional techniques or due to infected material being pushed beyond the root from the coronal aspects of canals.

In accordance with the present invention, after the root canal has been exposed, the root canal is cleaned progressively in sections with different instruments for the respective sections. By cleaning the root canal in sections, the instruments can adapt to the perimetrical anatomy of the root canal. As a result, the entire perimeter or substantially all of the perimeter is cleaned along the length of the root canal without substantially altering the configuration of the perimetrical anatomy. For example, a perimetrical anatomy that was primarily tubular or laminar will be enlarged and still be primarily tubular or laminar or at least there will not be a large round borehole corresponding to the diameter of the file superimposed on the original perimetrical anatomy. Additionally, the invention enables the practioner to prepare root canals in accordance with the anatomy of the root canal even though the practioner may not have been able to adequately identify the overall anatomy due to the inability to see the root canal from the mesial-distal view with common radiography. Further, the invention also enables the practioner to adapt to the contours of the root canal of all different types of teeth.

After the pulp chamber has been opened to expose the anatomical root canal, during the root canal therapy, the operative root canal is considered to include the anatomical root canal, which extends from pulp chamber or the floor of the pulp chamber to the apex, and the portion thereabove. The operative root canal is divided into three sections the operative coronal portion or access portion, the operative middle portion and the apical portion. After the operative coronal portion is adequately prepared, then the operative middle portion is cleaned and then the apical portion is cleaned.

To clean the operative middle portion of the operative root canal, a first instrument or set of instruments is provided. A second instrument or set of instruments is provided to clean the apical portion of the operative root canal after the operative middle portion of the root canal has been cleaned.

Each instrument in the first set of instruments comprises a handle connected to a file or a shaft with tines or an abrading portion. Each file has a length such that the operative middle portion of the operative root canal is cleaned without significantly removing pulp material from the apical root portion. Additionally, each file is designed to have a taper that is larger than the taper of each preceding file. Each file or shaft has an abrading portion for abrading the surfaces or walls of the root canal. In contrast to conventional files, as set forth in greater detail hereinbelow, the abrading portion may extend along the entire length of the file to enable the instrument to be used to clean the operative middle portion while also abrading the operative coronal portion.

The files are designed such that each file has sufficient flexibility to be flexed or curved to urge the abrading portion against the surfaces of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file is flexed or curved to urge the file, particularly the abrading portion, against the surfaces of the root canal.

After the operative middle portion of the operative root canal has been cleaned, the apical portion is cleaned with the second instrument or set of instruments. Each instrument in the second set of instruments comprises a handle connected to a file. Each file terminates at a tip and each file is configured with an abrading portion. Each file has a length sufficient to at least approximately reach the apex and to enable the abrading portion of the files to substantially contact and clean the pulp material in the apical portion of the root canal. The tip of the file is preferably rounded to prevent ledging.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

FIG. 4A is a longitudinal cross-sectional view of an extracted upper premolar to show the anatomy of the tooth from the buccal-lingual view.

FIG. 4B is a longitudinal cross-sectional view of the extracted upper premolar shown in FIG. 4A from the mesial-distal view.

FIG. 5A is a longitudinal cross-sectional view of an extracted lower incisor to show the anatomy of the tooth from the buccal-lingual view.

FIG. 5B is a longitudinal cross-sectional view of the extracted lower incisor shown in FIG. 5A from the mesial-distal view.

FIG. 25A is a longitudinal cross-sectional view of a tooth with a root canal that has been cleaned.

FIG. 25B is a longitudinal cross-sectional view of the tooth shown in FIG. 25A taken along cutting line 25B—25B to show that essentially all pulp material has been removed from the root canal.

FIG. 25C is an enlarged transverse cross-sectional view of the tooth shown in FIG. 25A taken along cutting line 25C—25C to show that the anatomy of the root canal has not been substantially altered by the cleaning thereof and to show the shaping of the canal in preparation of filling the root canal.

DETAILED DESCRIPTION OF THE PREFERRED EMBODIMENTS

The present invention relates to systems and methods for cleaning root canals through the removal of pulp material from the root canals. The invention provides for cleaning the root canal in progressive sections from crown to apex. After the pulp chamber is opened and preferably after further preparations, a first instrument or set of instruments is introduced into the root canal to clean a portion of the root canal and then the portion therebelow, the apical root portion, is cleaned with a second instrument or set of instruments. The invention enables a dental practitioner to remove and clean essentially all pulp material in a root canal requiring root canal therapy. The cleaning is achieved in a manner that is safer in terms of over thinning of the root canal and perforations and yet requires less instrumentation than conventional techniques.

Figures 18, 19A:
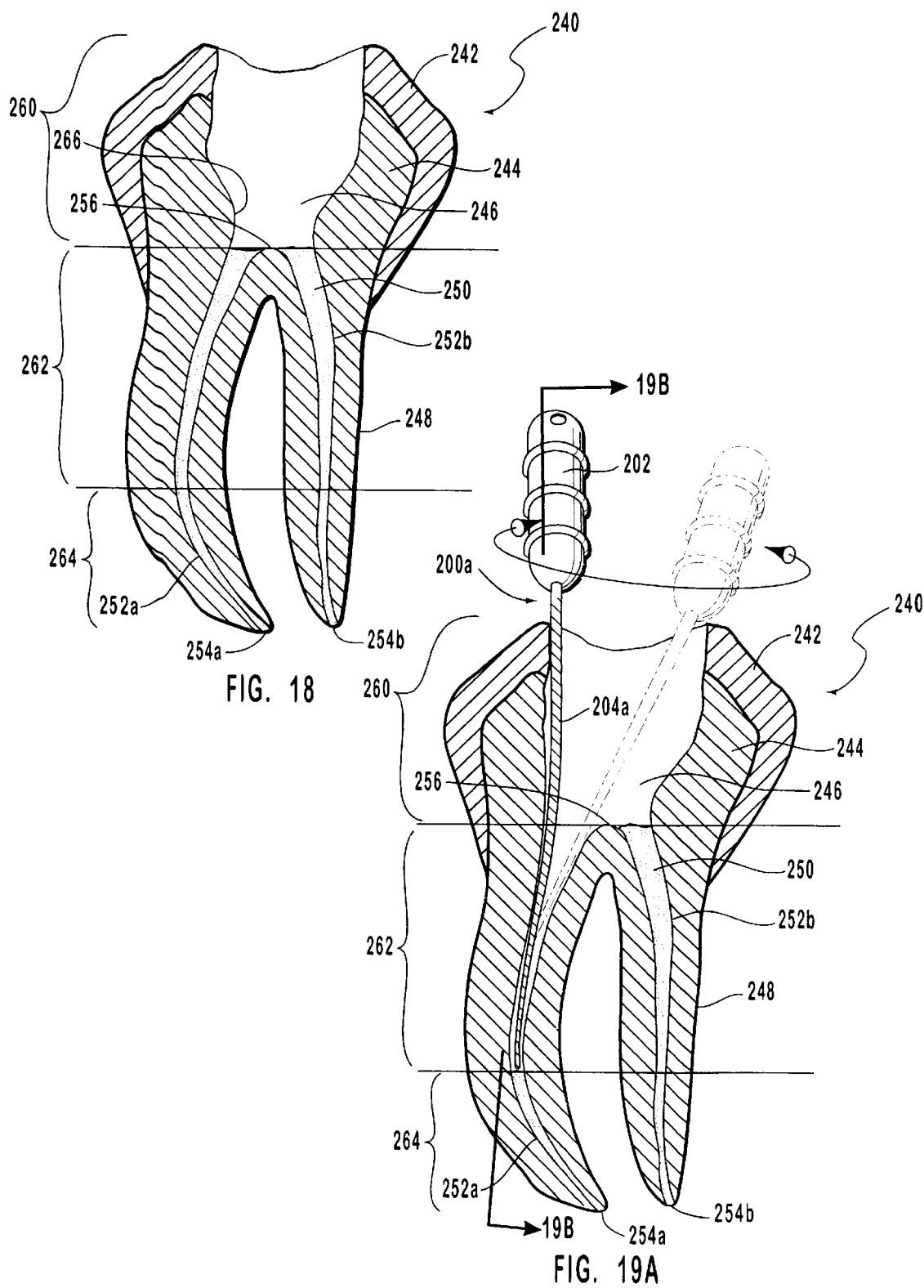
FIG. 18 is a longitudinal view of a tooth with an exposed pulp chamber.
FIG. 19A is a longitudinal cross-sectional view of a tooth with a file portion of a file instrument inserted into the root canal up to the apical portion.

The techniques described herein for progressive root canal therapy, from crown to apex, are essentially divided into three phases. The three phases correspond with three sections or portions of the operative root canal. After the pulp chamber has been opened to expose the anatomical root canal, during the root canal therapy, as shown in FIG. 18, the operative root canal is considered to include the anatomical root canal, which extends from the pulp chamber or the floor 256 of the pulp chamber 246 to the apex 254, and the portion thereabove. More specifically, the operative root canal comprises the operative coronal portion 260, the operative middle portion 262 and the apical portion 264. Operative coronal portion 260 essentially includes the access cavity walls. The operative middle portion 262 is the upper portion of the anatomical root canal while the apical portion 264 is the lower portion of the anatomical root canal.

The divisions of the operative root canal are distinguished from the nomenclature of the anatomical root canal as used to designate the sections before opening the tooth wherein the anatomical root canal is divided into the apical portion and the coronal portion. The coronal portion of the anatomical root portion is conventionally defined as the upper portion of the anatomical root canal which terminates at the floor of the pulp chamber. However, once the pulp chamber is exposed and instruments are introduced into the root canal, the opening into the tooth is merely an extension of the root canal as it is then a continuous chamber or open tract. Accordingly, the access walls are considered part of the operative root canal and are designated as the operative coronal portion or the access portion.

As indicated hereinabove, apical portion 264 extends from the apex of root canal 252 up to an area of anatomical root canal 252, such that the length of the apical portion is less than half of the length of the anatomical root canal as measured from the apex to floor 256. More specifically, apical portion 264 is generally the bottom one-third of the anatomical root canal 252. The actual length of the apical portion varies depending on many factors such as the type of tooth and the age of the tooth. However, the apical portion typically has a length in a range from about 3 mm to about 4 mm as measured from the apex.

As also indicated hereinabove, operative middle portion 262 is the top portion of the anatomical root canal 252 and extends from floor 256 down to an area of anatomical root canal 252, such that the length of the operative middle portion is greater than half of the length of anatomical root canal 252. More specifically, operative middle portion 262 is generally the top two-thirds of anatomical root canal 252 as measured down from floor 256. The length of operative middle portion can be estimated by identifying the overall length of the root canal, typically by use of radiography, and then subtracting about 3 mm to about 4 mm from the overall length.

Figure 16A:
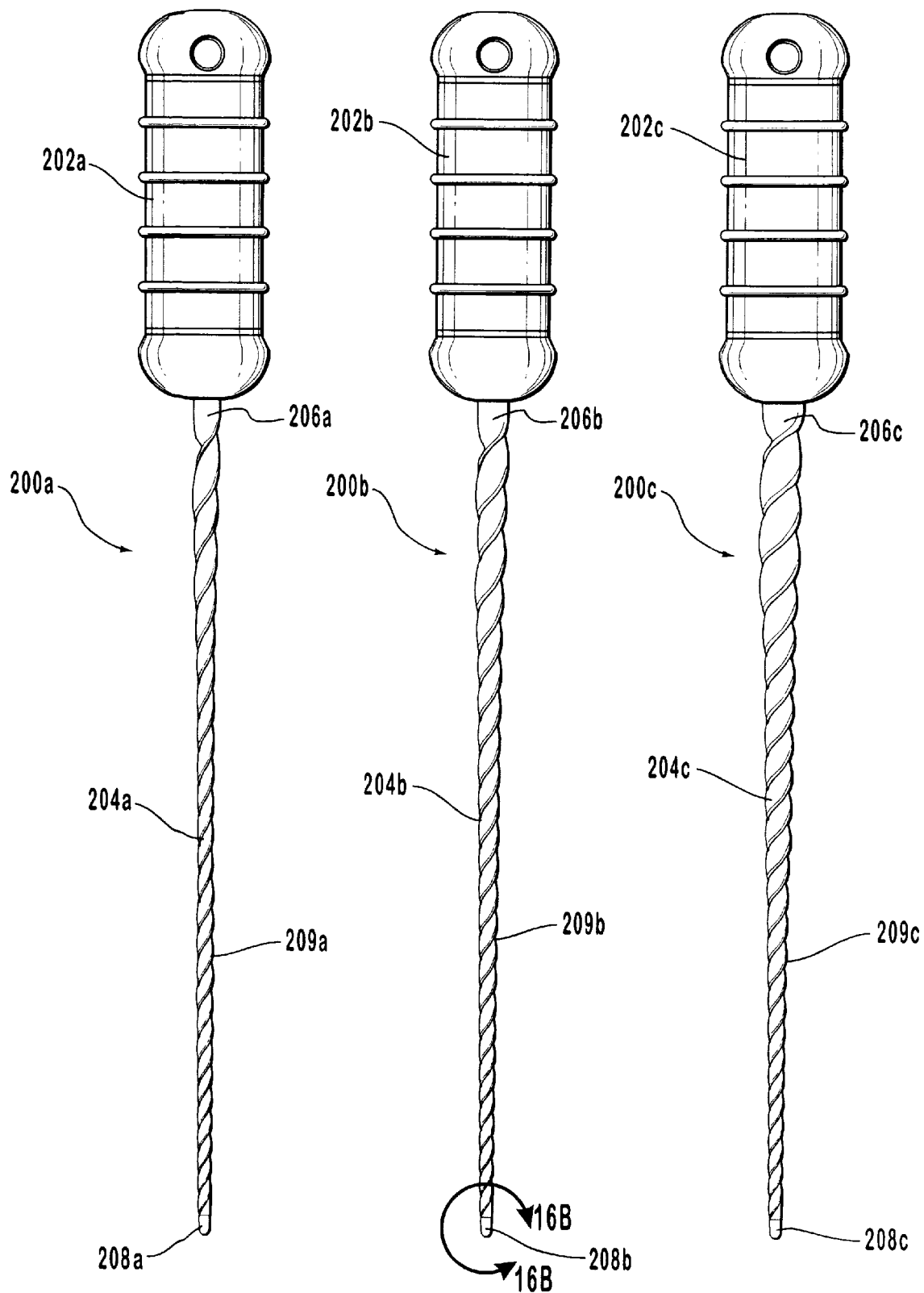
FIG. 16A is a perspective view of a set of endodontic instruments for cleaning of the coronal portion of a root canal.
Figures 16B, 17A, 17B, 17C:
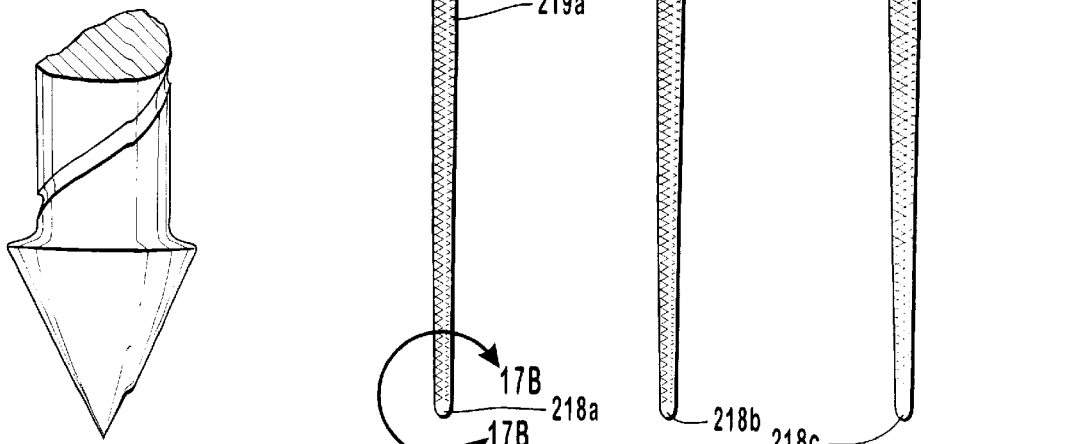
FIG. 16B is an enlarged perspective view of a tip of one of the files of an endodontic file instrument shown in FIG. 16A.
FIG. 17A is a perspective view of another embodiment of a set of endodontic instruments for cleaning of the coronal portion of a root canal.
FIG. 17B is an enlarged perspective view of a tip of one of the files of an endodontic file instrument shown in FIG. 17A.
FIG. 17C is another embodiment of a file tip of an endodontic file instrument.
Figure 21:
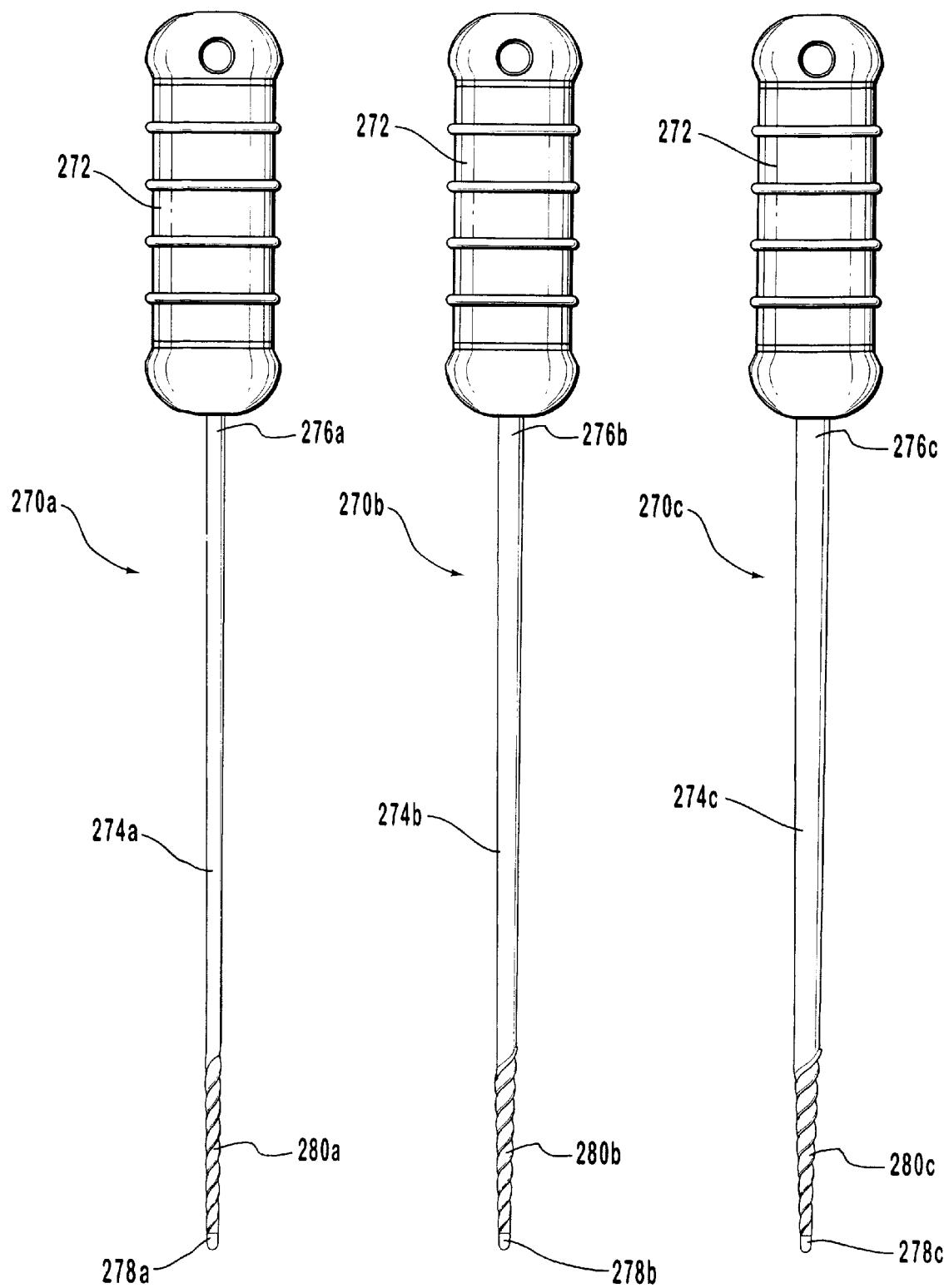
FIG. 21 is a perspective view of a set of endodontic instruments for cleaning the apical portion of a root canal.
Figure 22:
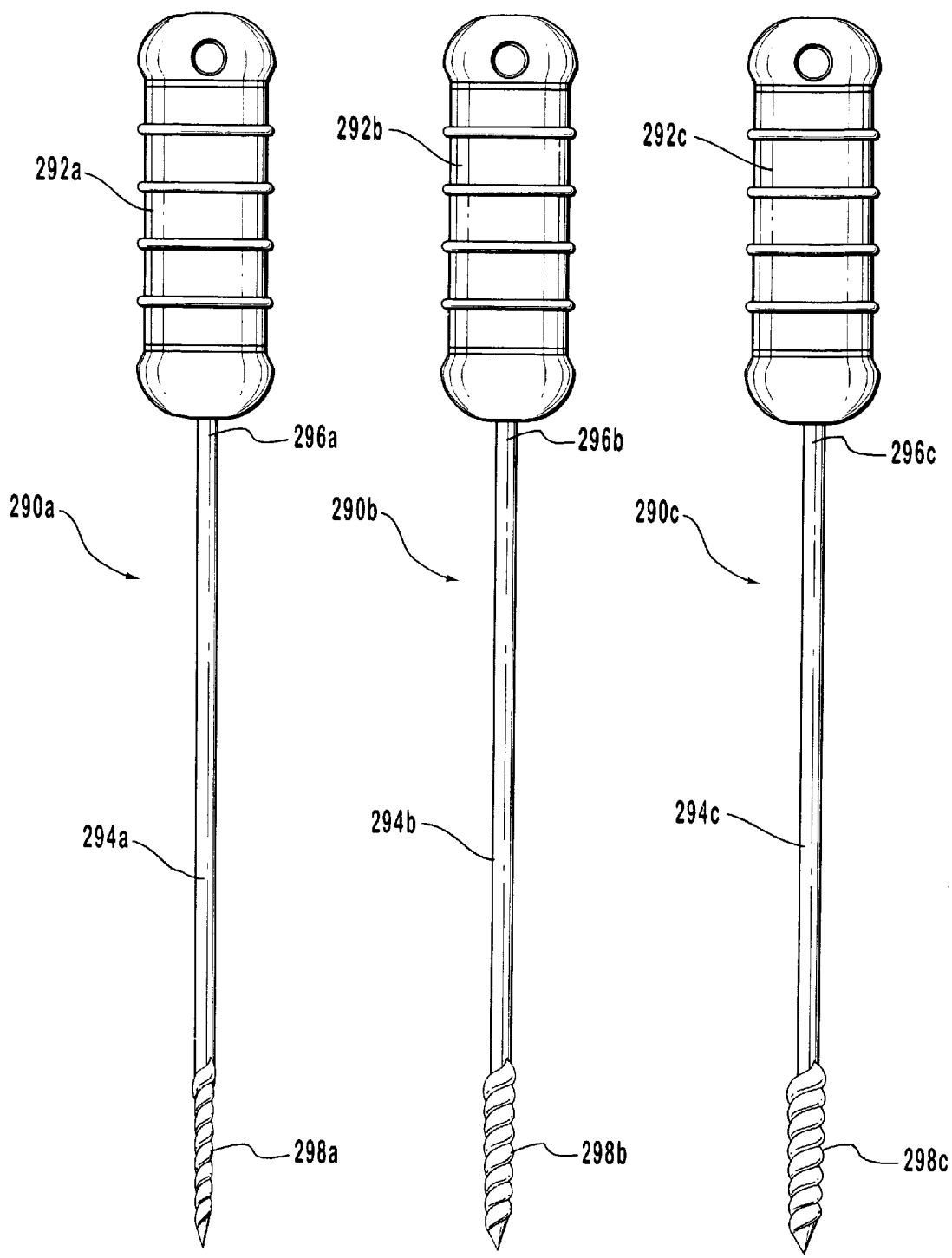
FIG. 22 is a perspective view of another embodiment of a set of endodontic instruments for cleaning the apical portion of a root canal.
Figure 23:
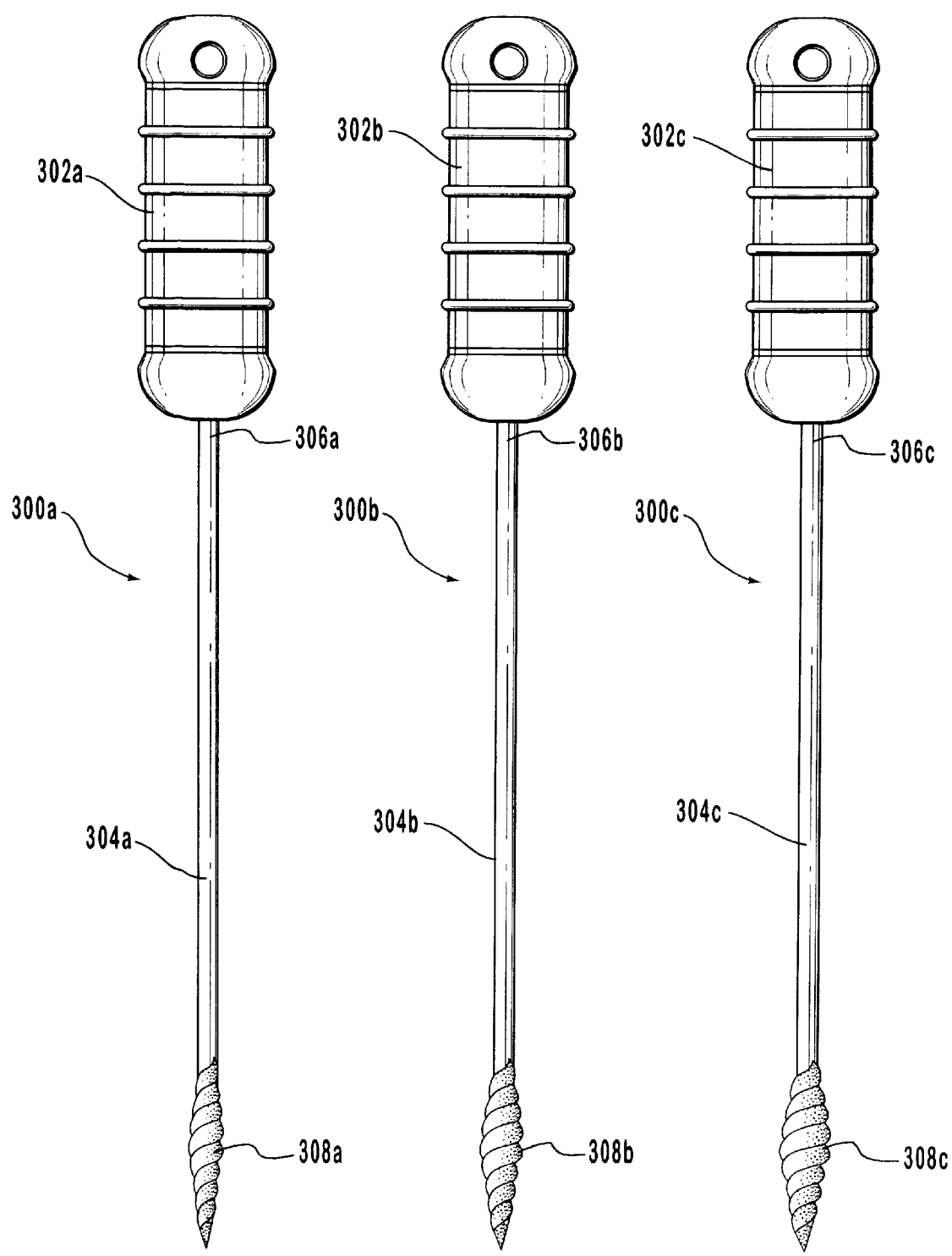
FIG. 23 is a perspective view of an additional embodiment of a set of endodontic instruments for cleaning the apical portion of a root canal.

As previously indicated, the three sections are treated in three primarily distinct sequential phases including: preparation of the operative coronal portion, then cleaning the operative middle portion and finally cleaning the apical portion. Examples of instruments intended for use in the cleaning the operative middle portion are shown in FIG. 16A and FIG. 17B. Examples of instruments intended for use in cleaning the apical portion are shown in FIGS. 21–23.

Figure 11A:
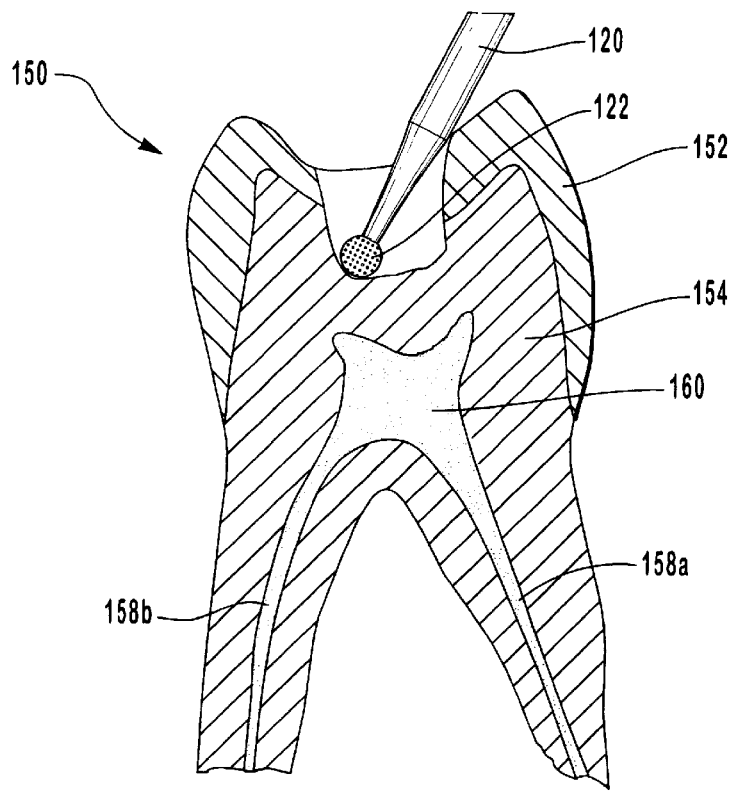
FIG. 11A is a longitudinal cross-sectional view of a burr being utilized to remove the overhanging enamel and dentin above the pulp chamber.
Figure 11B:
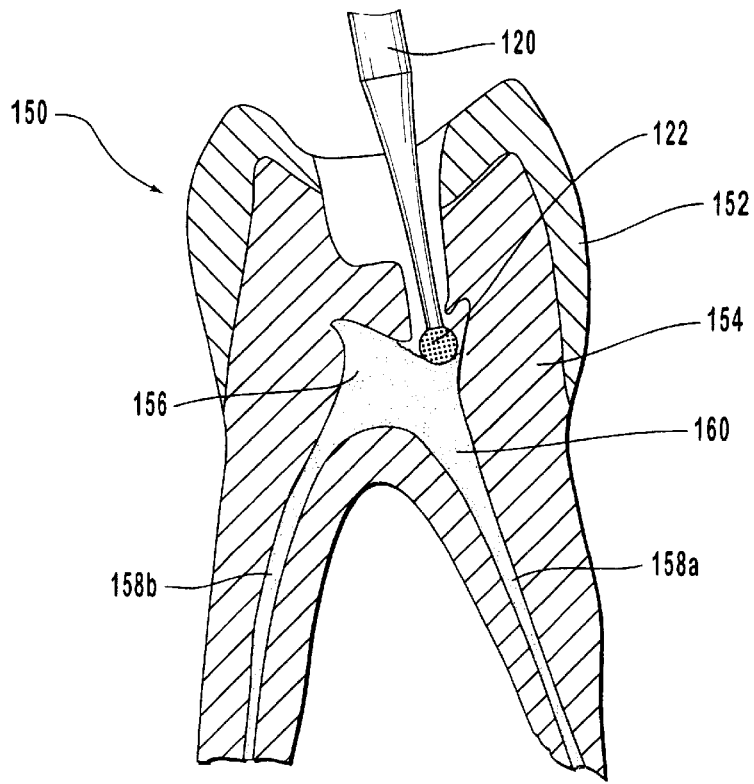
FIG. 11B is a longitudinal view of a burr extending through the enamel and the dentin into the pulp chamber.
Figure 12:
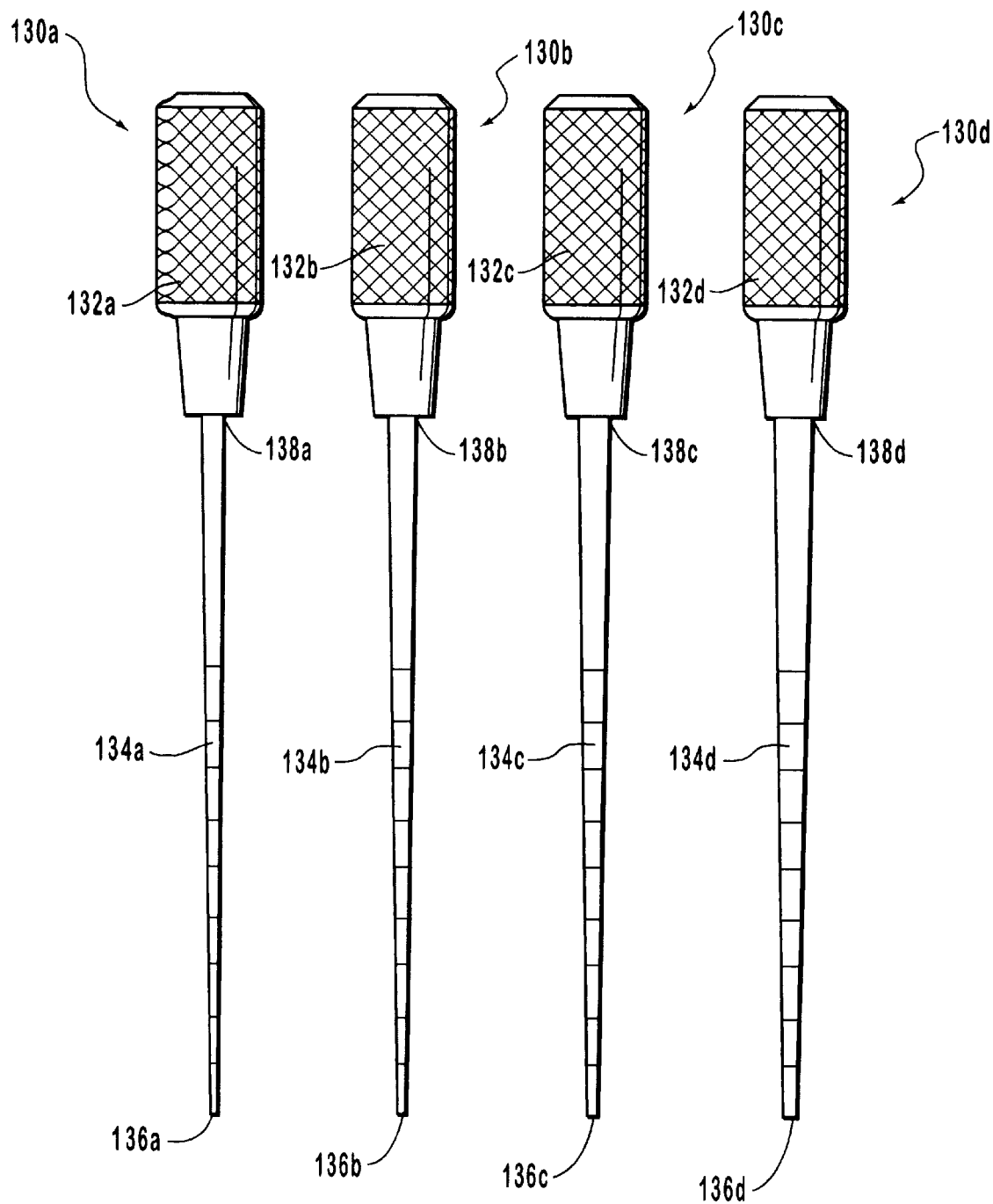
FIG. 12 is a perspective view of a prior art set of endodontic instruments utilized in the step-back technique.

The first phase or coronal phase involves exposing the pulp chamber and also preferably other steps to enhance accessibility into operative middle portion 262 and also apical portion 264. Accordingly, the coronal or access phase is initiated by exposing the pulp chamber. This can be achieved, for example, through the use of an instrument such as instrument 120 with bur 122 as shown in FIG. 11A and FIG. 11B, which is preferably a diamond bur used in conjunction with a low or high speed handpiece. However, any suitable instrument can be utilized such as those disclosed in Italian Patent No. 1,142,983 or Italian Patent No. 1,149,157, which are hereby incorporated by reference.

After the pulp chamber has been exposed and after the pulp material has been removed, a tooth appears as shown in FIG. 18 wherein a molar 240 is depicted with the overhanging portions of enamel 242 and dentin 244 removed to provide access into pulp chamber 246. Pulp material 250 still extends within root canal 252 from apices 254a and 254b to the floor 256 of pulp chamber 246. Also designated at 248 is the cementum of the tooth.

During the first phase, it is preferable to remove or reduce dentinal or enamel protrusion or irregularities that may obscure or hinder access of instruments into the remaining portions of the operative root canal. For example, dentinal shelves 266 depicted in FIG. 18 are preferably reduced or rectified to provide greater access for instrumentation during the subsequent phases. Accordingly, in the subsequent related drawings, such as FIG. 19A, the dentinal shelf is shown removed on the canal being cleaned and as not being yet removed above the other canal. Rectification or regularization can be achieved by any suitable means. An example of a means for rectifying dentinal shelves is set forth in U.S. Pat. No. 5,642,998 which was incorporated by reference hereinabove. It may also be necessary to widen operative coronal root canal. Some dentists may prefer obtaining greater access through a cuspidectomy.

During this phase as well as the others, it is generally necessary to utilize irrigants. Any irrigation means can be utilized. However, it is preferable to utilize an irrigation tip as set forth in copending U.S. patent application Ser. No. 09/014,764 entitled Endodontic Irrigator Tips and Kits and filed by Francesco Riitano concurrently herewith on Jan. 28, 1998; the disclosure of which is hereby incorporated by reference. During the procedure, a rubber dam is typically used to isolate the tooth, which may require in some instances, the rebuilding of the pulp chamber walls.

After the operative coronal portion has been adequately prepared, it is preferable to prepare a x-ray image of the tooth to identify the length of the operative root canal for use in identifying the preferred working length for the instrument or set instruments to used in the next phase. The preferred working length is preferably identified by subtracting about 3 mm from the total radiographic length of the operative root canal. The total radiographic length is preferably derived from a radiograph made using a localizator and a long cone radiographic head.

The second phase involves cleaning operative middle portion 262. It may also involve to some extent further rectification of the operative coronal or access portion 260 through further removal of any ledges or outcroppings which prevent straight and easy access into the operative middle portion 262. Additionally, it may also involve some degree of rectification of the upper region of operative middle portion 262.

An example of a set of instruments designed for cleaning the operative middle portion is shown in FIG. 16A. The set comprises three file instruments 200 which each comprise a handle 202 connected to a file 204 or a shaft with tines or an abrading portion. Each file 204 has a top end 206 where the file joins handle 202. Handle 202 is connected to top end 206 of file 204 such that movement of handle 202 also moves at least top end 206 of file 204 along a common longitudinal axis with handle 202.

The diameter of top end 206a is less than the diameter of top end 206b and the diameter of top end 206b is less than the diameter of top end 206c. When utilized to clean the operative middle portion of a root canal, file 200a is first introduced into the operative middle portion followed by file instrument 200b and then 200c. Accordingly, the diameter of the top end of each successive file introduced into the operative middle portion is greater than the diameter of the top end of each preceding file.

Each file terminates at a tip 208 located opposite top end 206. The diameter of each tip 208 remains substantially constant such that the diameter of tip 208a is about the same as the diameter of tip 208b and tip 208c. Alternatively, the tip diameter may vary between instruments in a set such that, for example, the tip diameter of each sequentially inserted file is progressively larger. As shown in FIG. 16B, which is an enlarged view of tip 208b, the tips are generally sharp and are configured for at least minimal cutting capability.

Each operative middle portion file 204 is configured with a suitable abrading portion 209 along most or all of the length of each file. Abrading portion 209 is at least the outer edge of the file 204. The abrading portion of the files in FIG. 16A are formed by twisting a blank such as a rectangular blank.

FIG. 17A depicts another set of file instruments 210 which have files with a different abrading portion compared to the abrading portion of the files of file instruments 200. The files 214 have abrading portions 219 that were formed by machining the files to have knurled surfaces. Abrading portion 219 as well as abrading portion 209 and the other abrading or cleaning surfaces disclosed herein are examples of means for abrading the root canal.

FIG. 17B is an enlarged view of tip 218a which is shown with a more rounded configuration than tip 208b such that the tip has essentially no cutting capability. FIG. 17C shows another embodiment of a suitable tip which is designed for more aggressive cutting than tip 208b at least as the tip is pushed downward.

Since the tip diameters are essentially equal and since the diameter of the top end of each successive file introduced into the operative middle portion is larger than the diameter of the top end of the preceding file, the taper of each successive file in the set is larger than the preceding file. Each successive file accordingly has an increased surface area for cleaning the root canal. Additionally, as files are inserted into a root canal with larger and larger tapers, the rigidity of the upper half of each successive file also increases. The increase in rigidity is, however, minimized by maintaining the tip of each file at about the same diameter. The flexibility of the lower half remains essentially constant. The rigidity in the upper half is used to remove interferences and to properly rectify the operative coronal portion 260 and the operative middle portion 262.

By properly selecting a combination of factors including the diameters of the files at the top ends and at the tips as well as the material used to form the files, the files are designed such that each file has sufficient flexibility to be flexed or curved to urge the abrading portion against the surfaces or walls of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file instrument is flexed or curved to urge the abrading portion against the surfaces of the root canal.

The file can be formed from any suitable material. In forming a suitable file, the material is preferably selected in view of the dimensions and design, to yield a file having the desired properties with respect to flexibility, resilience and/ or rigidity as set forth above. The preferred material for forming files used to clean the operative middle portion of root canals is stainless steel. Other metals can also be used such as nickel/titanium; however, it may be necessary to design the files to have larger diameters than files formed from stainless steel when using nickel/titanium as nickel/ titanium tends to be more flexible than steel. Alternatively, the files can be formed from suitable non-metal materials, such as a plastic.

The length of each file used to clean the operative middle portion depends on the tooth being cleaned. However, the length is generally in a range from about 8 mm to about 35 mm, more preferably in a range from about 10 mm to about 30 mm and most preferably in range from about 14 mm to about 26 mm. When the files are formed from stainless steel or a material with comparable properties, the top end diameter of each file is in a range from about 0.25 mm to about 2 mm, preferably from about 0.3 mm to about 1.8 mm and most preferably from about 0.4 mm to about 1.5 mm. Additionally, when the files are formed from stainless steel or a material with comparable properties, the tip diameter of each file is in a range from about 0.06 mm to about 0.4 mm, preferably from about 0.08 mm to about 0.3 mm and most preferably from about 0.1 mm to about 0.25 mm.

After identifying the operative middle portion length and removing the overhanging enamel 242 and dentin 244, the practitioner selects a file instrument or a set of file instruments as shown in FIG. 16A or FIG. 17A with a file length corresponding to the operative middle portion length. As shown in FIG. 19A, file 204a of file instrument 200a is then inserted into root canal 252 down through operative middle portion 262 without extending substantially into apical portion 264. Each file 204 of each file instrument 200 in the set of instruments shown in FIG. 16A has a length that is only sufficient to enable the file to contact the operative middle portion of the root canal. Accordingly, a file instrument such as file instrument 200a or a set of file instruments such as 200a, 200b and 200c comprises a first endodontic instrument means for anatomical removal and anatomical cleaning of essentially all pulp material from the operative middle portion without significantly removing pulp material from the apical root portion.

The file length of files 204 enables a practitioner to aggressively clean the operative middle portion without worrying that the instrument will overly thin the root canal, perforate the apex or that cleaning will cause extrusion of material through the apex. Another benefit of cleaning the operative middle portion first is that the apical portion is then generally more accessible and easily cleaned.

Figure 19B:
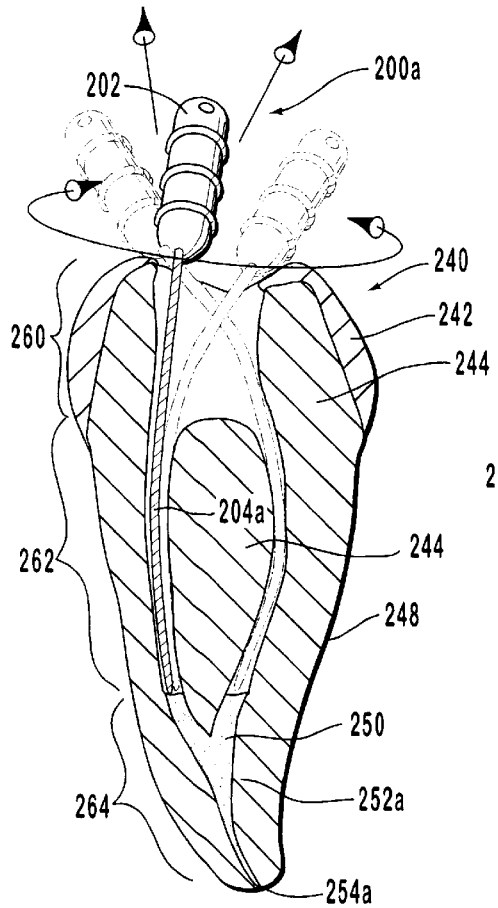
FIG. 19B is a longitudinal cross-sectional view of the tooth shown in FIG. 11A taken along cutting line 19B—19B to depict the cleaning of the pulp material from the coronal portion of the root canal.

By beginning at the operative middle portion, the practitioner can use an instrument that is relatively flexible compared to the instruments typically used to clean the operative middle portion after cleaning the apical portion. As shown in FIG. 19B, which is a cross-sectional view taken along cutting line 19B—19B of tooth 240 in FIG. 19A, file 204a of file instrument 200a is sufficiently flexible to be flexed against any surface of operative middle portion 262 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal.

File instrument 200a is shown in FIGS. 19A and 19B being moved in a longitudinal movement or up and down movement as well as being rotated while file 204a is flexed or arched to urge the file against the root canal surfaces. As shown, the configuration of the files used to clean the operative middle portion enable a practitioner to move the files from side to side or around the perimeter. In contrast to prior art methods which limited the practitioner to essentially rotating a conically shaped file to yield a cone shaped borehole, the file has more than one center of motion during cleaning of the operative middle portion of the root canal, such as a pivot point or center of rotation, as the tip of the file or at least a part of the abrading portion does not generally remain primarily in one position.

Due mainly to the configuration of the files, a practitioner can use the contours of the root canal as a guide for the movements of the files as the files are pushed against the surfaces of the root canal and simultaneously moved around the perimeter or periphery of the root canal until the practitioner has reached the beginning location of the cleaning and shaping process. For example, in root canals that are primarily noncircular, the files can be urged along one side and then along the next side wall in a manner such that the resulting cleaned and shaped root canal is generally widened but still primarily noncircular. In other words, there is essentially no borehole that obviously corresponds to the shape of the file.

Due to the ability to move the file as discussed, the anatomy of the root canal remains substantially unaltered despite the cleaning of essentially all pulp material from the operative middle portion. Knowing that the final anatomy is guided by the shape of the original anatomy enables a practitioner to more confidently urge a file such as file 204a against all surfaces of root canal 252 and aggressively clean all of the surfaces of operative middle portion of the root canal since the likelihood of overly thinning the root canal or lateral perforations as shown in FIGS. 15A–C and FIG. 15E is diminished.

Figure 13A:
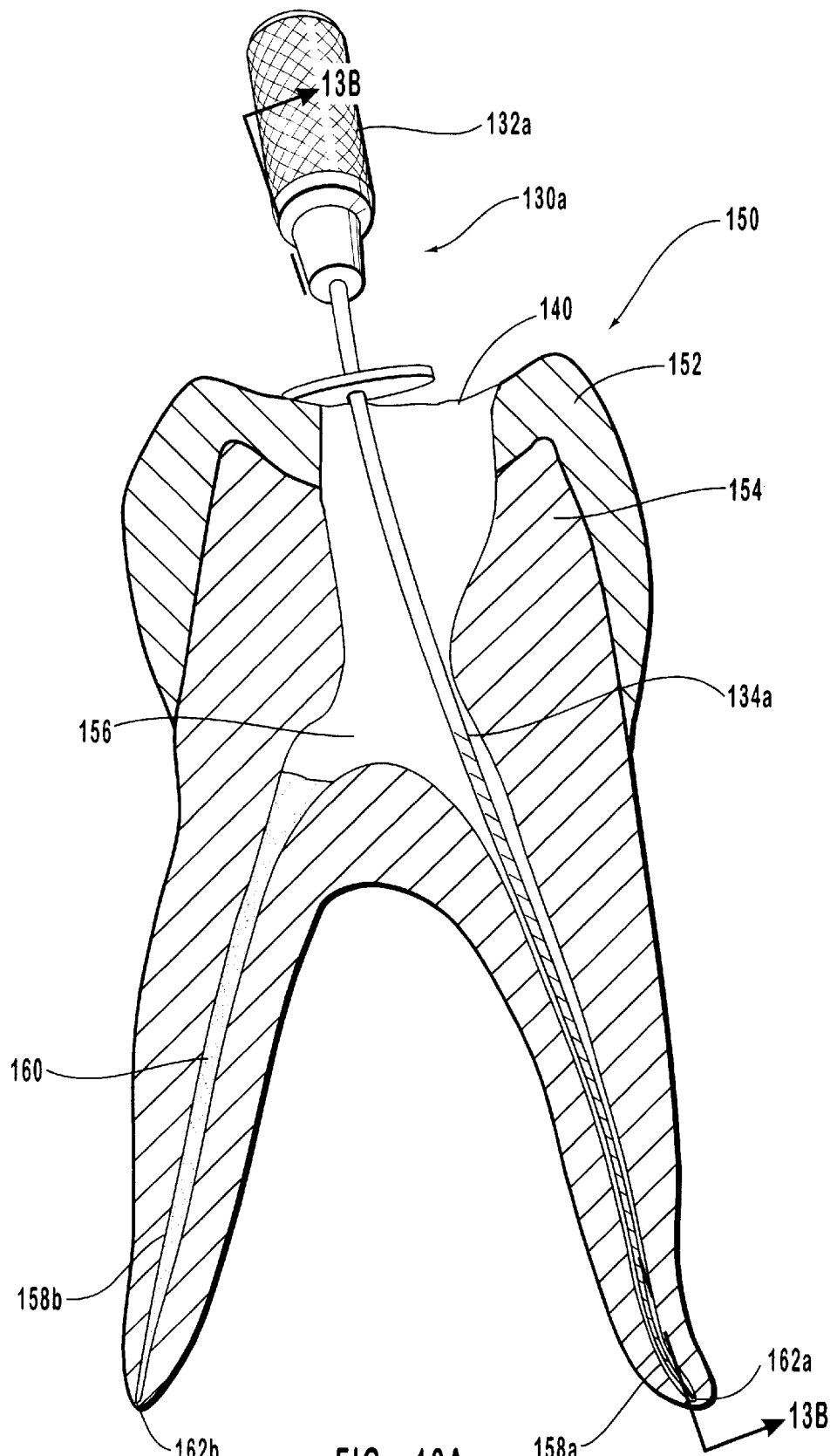
FIG. 13A is a longitudinal cross-sectional view of a tooth being cleaned with a file instrument used in the step-back technique.
Figure 13B:
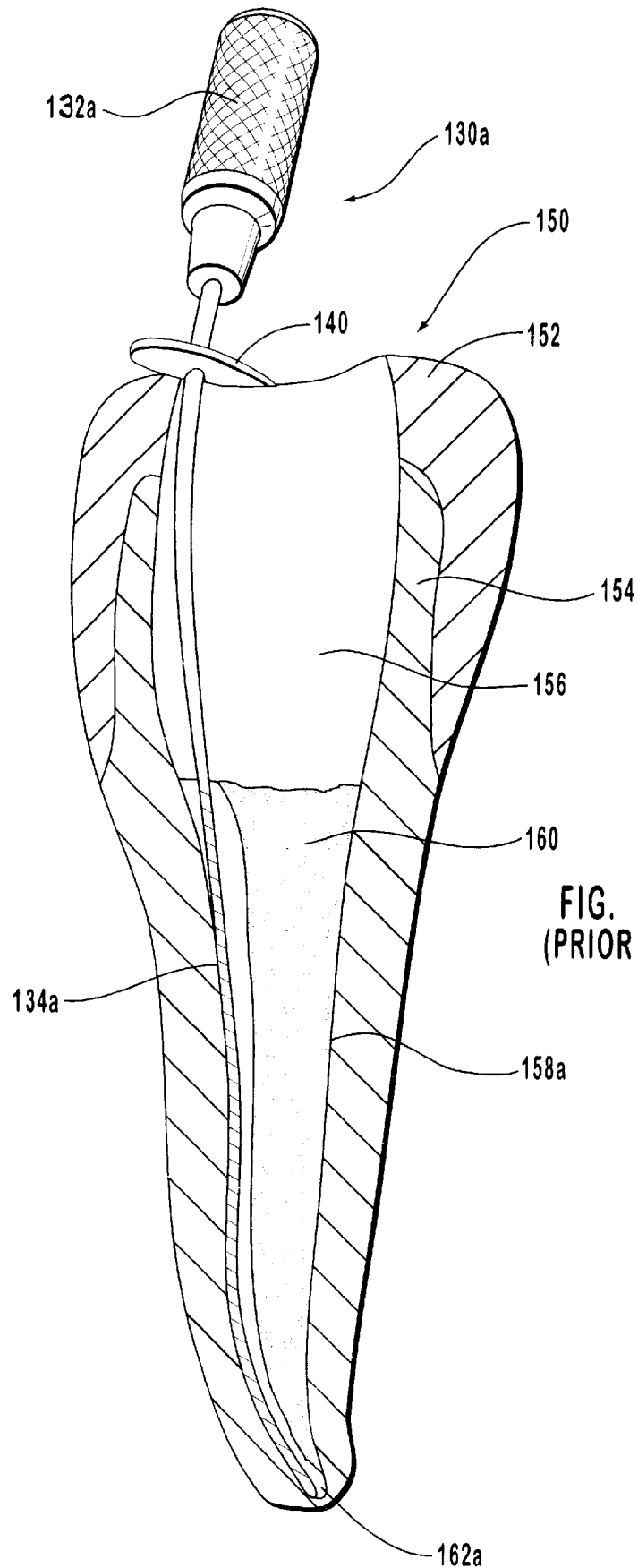
FIG. 13B is a longitudinal cross-sectional view of the tooth shown in FIG. 4A taken along cutting line 13B—13B, which shows the portion of the root canal which cannot be viewed in vivo.
Figures 14A, 14B:
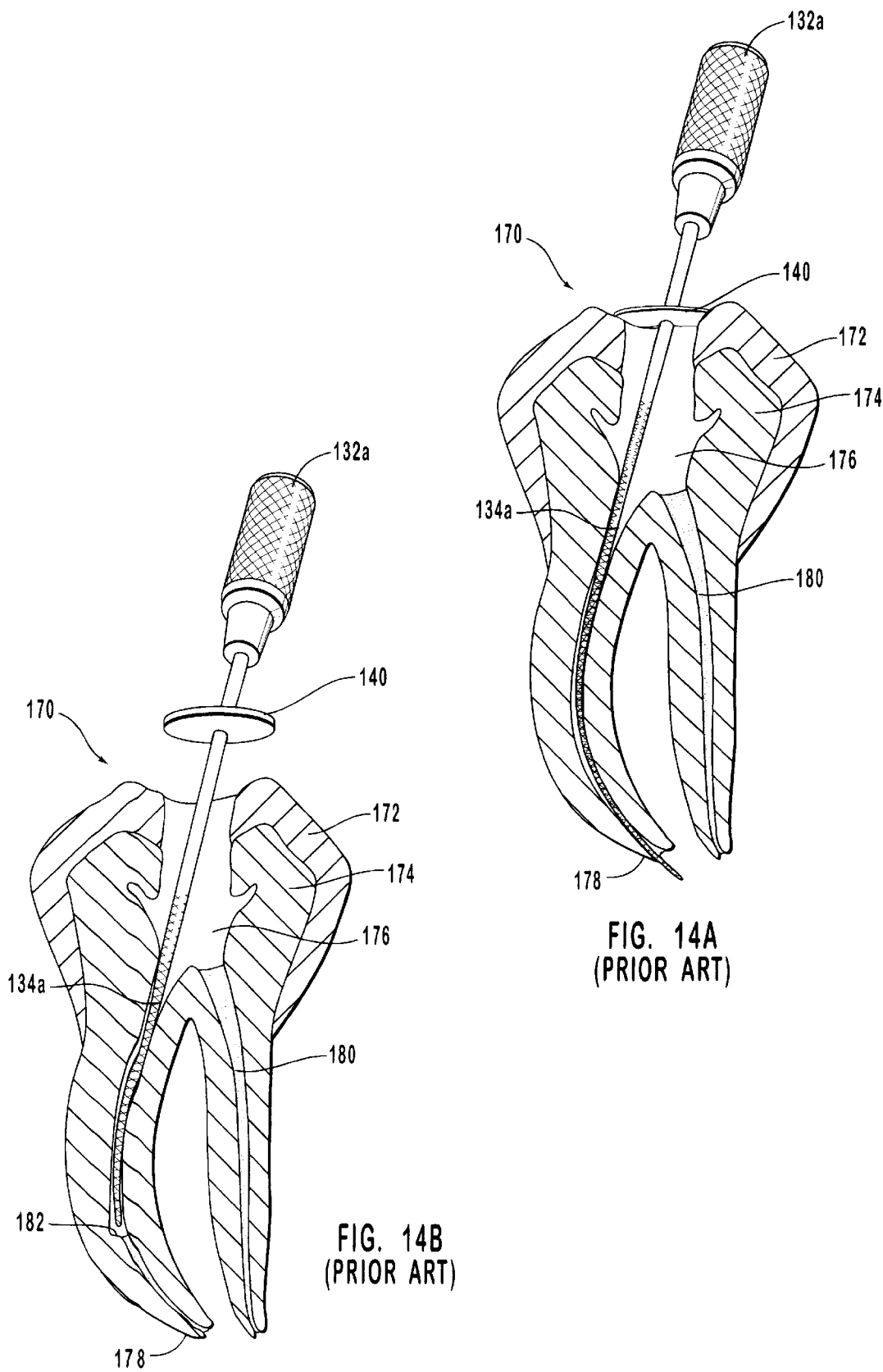
FIG. 14A is a longitudinal cross-sectional view of a tooth depicting apical perforation during cleaning of the root canal.
FIG. 14B is a longitudinal cross-sectional view of a tooth depicting ledging during cleaning of the root canal.

Another advantage of the configuration of use of operative middle portion instruments such as file 204a is that the file can simultaneously abrade both operative coronal portion 260 and operative middle portion 262. The files can simultaneously abrade both portions as the file can have an abrading portion along the entire length of the file, which is in contrast to files formed in accordance with ISO standardization. Files formed in accordance with ISO standardization have abrading portions of up to 16 mm and the remainder of the file is a smooth shank. Since such conventional files are inserted down to the apex, it is generally not possible to abrade any portion beyond the anatomical root canal. A further problem posed by such configurations results from the frequent failure to remove interferences extending from the access or root chamber above the anatomical root canal. As a result the instrument must flex around the interferences as shown in FIG. 13A which further increases the likelihood of wall perforations, overthinning and failing to clean significant portions of the canal. It especially increases the likelihood of iatrogenic modifications resulting from the tip of the file.

File instrument 200a is preferably used in conjunction with an instrument designed for movement of endodontic file instruments. File instrument 200a can be continuously rotated in one direction only or file instrument 200a can be rotated in a reciprocating motion such that file instrument 200a rotates for example, clockwise for half of a revolution and then counterclockwise for half a revolution. A reciprocating motion is preferred as such motion enables the file to alternately engage material 250 and the walls of the operative middle portion of the root canal in a manner that removes material 250 and to then rotate in the opposite direction such that the file less aggressively engages material 250 and the operative middle portion walls, depending on the file design. Accordingly, rotating file instrument 200a in reciprocating motion minimizes breakage of file 204a when file 204a encounters a surface that prevents rotation of file instrument 200a in a direction that enables cleaning and removal of material 250. File instrument 200a can also be vibrated or manipulated by hand. Hand milling is, however, more difficult and time consuming.

Figure 20A:
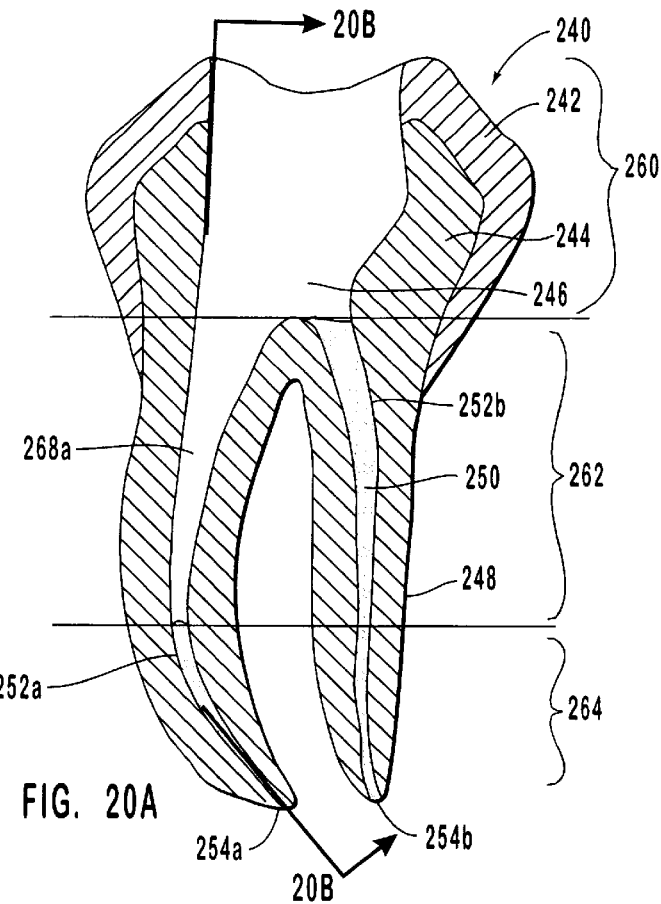
FIG. 20A is a longitudinal cross-sectional view of a tooth depicting a coronal portion of a root canal which has been cleaned by the removal of the pulp material.
Figure 20B:
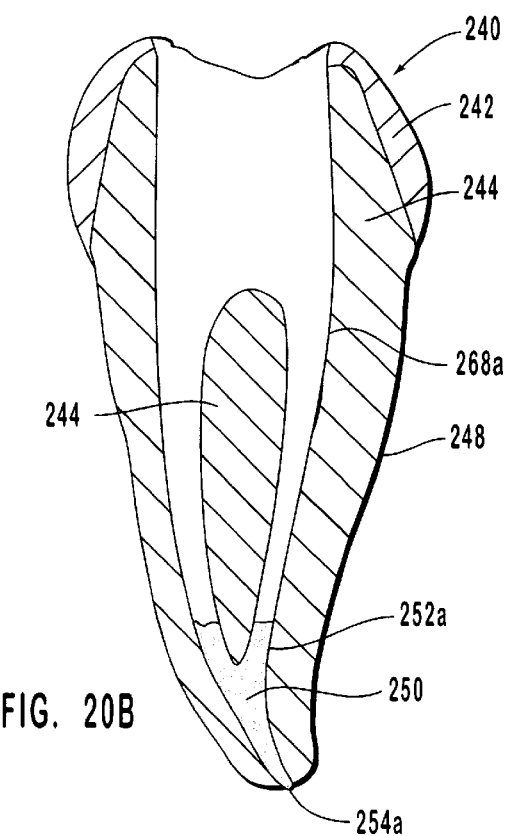
FIG. 20B is a longitudinal cross-sectional view of the tooth shown in FIG. 20A to show that essentially all pulp material has been removed from the coronal portion of the root canal.

FIG. 20A shows a cross-sectional view corresponding to the x-ray view after pulp material 250 has been removed from the operative middle portion 262 of root canal 252a and after the surfaces of root canal 252a have been shaped to yield shaped surfaces 268a of the root canal. FIG. 20B is a longitudinal cross-sectional view taken along cutting line 20B—20B of tooth 240 in FIG. 20B which clearly shows that essentially all pulp material has been removed and cleaned from operative middle portion 262.

Removal of pulp material 250 from operative middle portion 262 removes the majority of bacteria in the pulp canal since the majority of bacteria in an infected root canal is typically located in the operative middle portion. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion significantly reduces the likelihood of such complications. Additionally, by removing the majority of bacteria before cleaning the apical portion, the likelihood of successful root canal therapy is increased in several other ways. The apical portion is more delicate compared to the operative middle portion and is therefore more likely to be the site of problems such as overly thinning the root canal, apical perforation or apical extrusion. On this basis, if problems occur, less material remains in the root canal to cause postoperative complications.

To minimize the possible introduction of bacteria, it is preferable to utilize a kit such as the kit disclosed in copending U.S. patent application Ser. No. 09/014,765 entitled Containing Device For Dental Tools with Foam Supporting Materials and filed by Francesco Riitano concurrently herewith on Jan. 28, 1998; the disclosure of which is hereby incorporated by reference. The kits preferably support several instruments with identical lengths positioned to be easily grasped and preferably in an antimicrobial solution.

It should be noted that when there is an atresic root canal, it is preferable to use EDTA in a hydrosoluble gel and leave the composition in the canal for a few minutes.

Figure 33A:
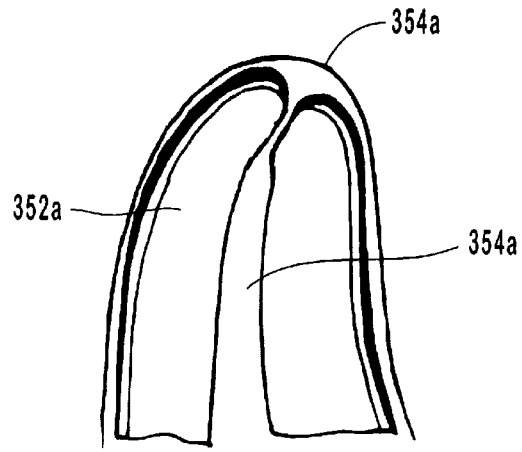
FIG. 33A is an enlarged perspective view of x-ray image of a root canal of a vital tooth without periapical rarefaction.
Figure 33B:
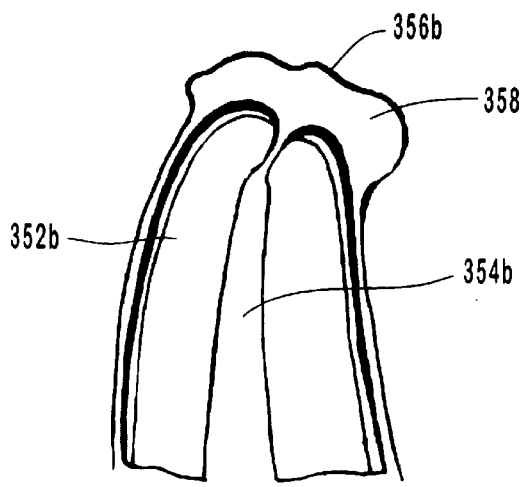
FIG. 33B is an enlarged perspective view of a x-ray image of a root canal of an infected root canal without periapical rarefaction.
Figure 33C:
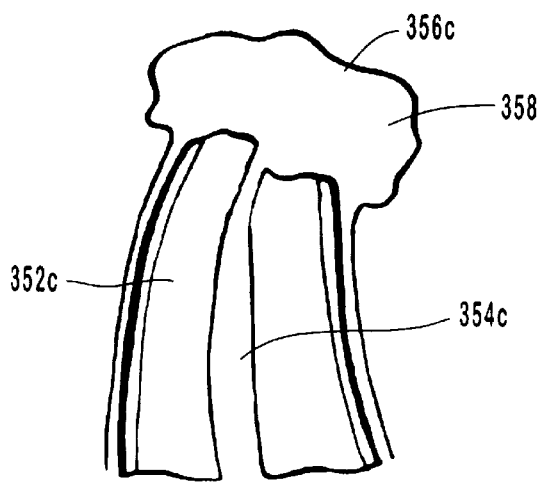
FIG. 33C is an enlarged perspective view of a x-ray image of a root canal of an infected root canal with apical and periapical resorption.

The third phase, cleaning of the apical portion, is preferably begun after obtaining further x-ray images while an apical instrument is inserted into a root canal to determine the desired working length of the instrument. In establishing the working length, the state of the apex and the periapical tissues should also be considered. The states most frequently shown in radiography are shown in FIGS. 33A–C wherein the apical portion of root canals 354a–c of roots 352a–c are depicted. FIG. 33A depicts a root canal 354a of a vital tooth without periapical rarefaction as shown by the normal border with the bone at 356a. FIG. 33B depicts an infected root canal 354b without periapical rarefaction as shown by radiolucency 358b. FIG. 33C depicts an infected root canal 354c with apical and periapical resorption as shown by radiolucency 358c. Depending on whether the practioner identifies the condition of the root canal as being that depicted in FIG. 33A, FIG. 33B or FIG. 33C, the working length is respectively in a range from about 0 to about 2 mm, about 1.5 mm or about 0.5 mm shorter than the distance from the occlusal surface to the radiographic apex of the tooth.

An example of a set of instruments designed for removing and cleaning of essentially all remaining pulp material from the apical portion of a root canal is shown in FIG. 21. The set comprises three file instruments 270a, 270b and 270c. Each file instrument comprises a handle 272 connected to a file 274. Each file 274 has a top end 276 where the file joins handle 272. When utilized to clean the apical root portion of a root canal, file 270a is first introduced into the apical root portion followed by file 270b and then 270c. Each file terminates at a tip 278 located opposite top end 276. A file instrument such as file instrument 270a or a set of file instruments such as 270a, 270b, and 270c comprises a second endodontic instrument means for removal and cleaning of essentially all remaining pulp material from the apical root portion after the pulp material has been essentially removed from the operative middle portion.

Tips 278a–c can have any configuration, however, tips 278a–c preferably have minimal cutting capability to decrease the likelihood of ledging. An example of a suitable configuration for tips 278a–c that is designed to minimize the cutting ability of the tips is that of the round tip shown in FIG. 17B.

Each file 274 of the file instruments designed for cleaning the apical root portion of a root canal is configured to have an abrading portion 280 along at least a portion of the length of file 274. The entire length of each file 274 can be configured with an abrading portion 280, however, abrading portion 280 preferably extends from tip 278 part way upward towards top end 276 such that the remainder of file 274 is relatively smooth. More particularly, each file is preferably configured with an abrading portion along less than about half of the length of the file and more preferably about one-third of the length between tip 278 and top end 276. The abrading portion 280 can have a similar or identical configuration to the abrading portion of the file or files used to clean the operative middle portion of the root canal.

The length of a file such as files 274a, 274b and 274c is sufficient such that when the files are inserted into the root canal the tips can at least approximately reach the apex and the abrading portion 280 of the files can substantially contact and clean the pulp material in the apical portion of the root canal. Such file lengths are typically within a range from about 8 mm to about 35 mm, more preferably in a range from about 14 mm to about 35 mm and most preferably in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm.

The diameter of the abrading portion is generally within a range from about 0.06 mm to about 1.4 mm. As shown in FIG. 21, each successive file has an abrading portion, 280a, 280b, and 280c which is successively larger in diameter than the abrading portion of the preceding file. Additionally, the taper of files 274 from tip 278 to top end 276 is preferably constant as shown in FIG. 21. However, the diameter at top end 276, in addition to being greater than the diameter of the abrading portion, can also be equal to or less than the diameter of abrading portion 280 or tip 278. Further, the tip diameter of each file may be approximately equal as shown in FIG. 21 or increase sequentially as shown in FIG. 21.

The abrading portion 280 of each file 274 of file instruments 270 is formed by twisting a blank to spiral the blank. The abrading portion 280 preferably has few spirals such that the action of abrading portion 280 against the walls or surfaces of the apical portion of the root canal is relatively gentle. Such an abrading portion is less aggressive as fewer spirals results in tines that have a wider angle.

FIG. 22 depicts an alternative embodiment of files configured for cleaning the apical portion of a root canal. The set of instruments depicted in FIG. 22 comprises three file instruments 290a, 290b and 290c. Each file instrument comprise a handle 292 connected to a file 294. Each file 294 has a shank portion 296 above an abrading portion 298. Shank portion 296a has substantially the same diameter along its length and the diameter of shank portion 296a is approximately the same as the diameter of shank portion 296b and 296c. The diameter of abrading portion 298a is essentially constant along the length of abrading portion 298a. Similarly, abrading portions 298b and 298c also have substantially constant diameters. The diameter of abrading portion 298b is larger than the diameter of abrading portion 298a and the diameter of abrading portion 298c is larger than the diameter of abrading portion 298b.

FIG. 23 depicts an additional alternative embodiment of files configured for cleaning the apical portion of a root canal. The set of instruments depicted in FIG. 23 comprises three file instruments 200a, 200b and 200c. Each file instrument comprise a handle 202 connected to a file 204. Each file 204 has a shank portion 206 above an abrading portion 208. Shank portion 206a has substantially the same diameter along its length and the diameter of shank portion 206a is approximately the same as the diameter of shank portions 206b and 206c. Each abrading portion 208 extends from each respective shank portion 206 with a shape that is generally elliptical. Additionally, the width of each successive abrading portion 208 is larger than that of the preceding abrading portion. More specifically, the width of each successive abrading portion is larger at its midpoint than at the midpoint of the preceding abrading portion.

Figure 24:
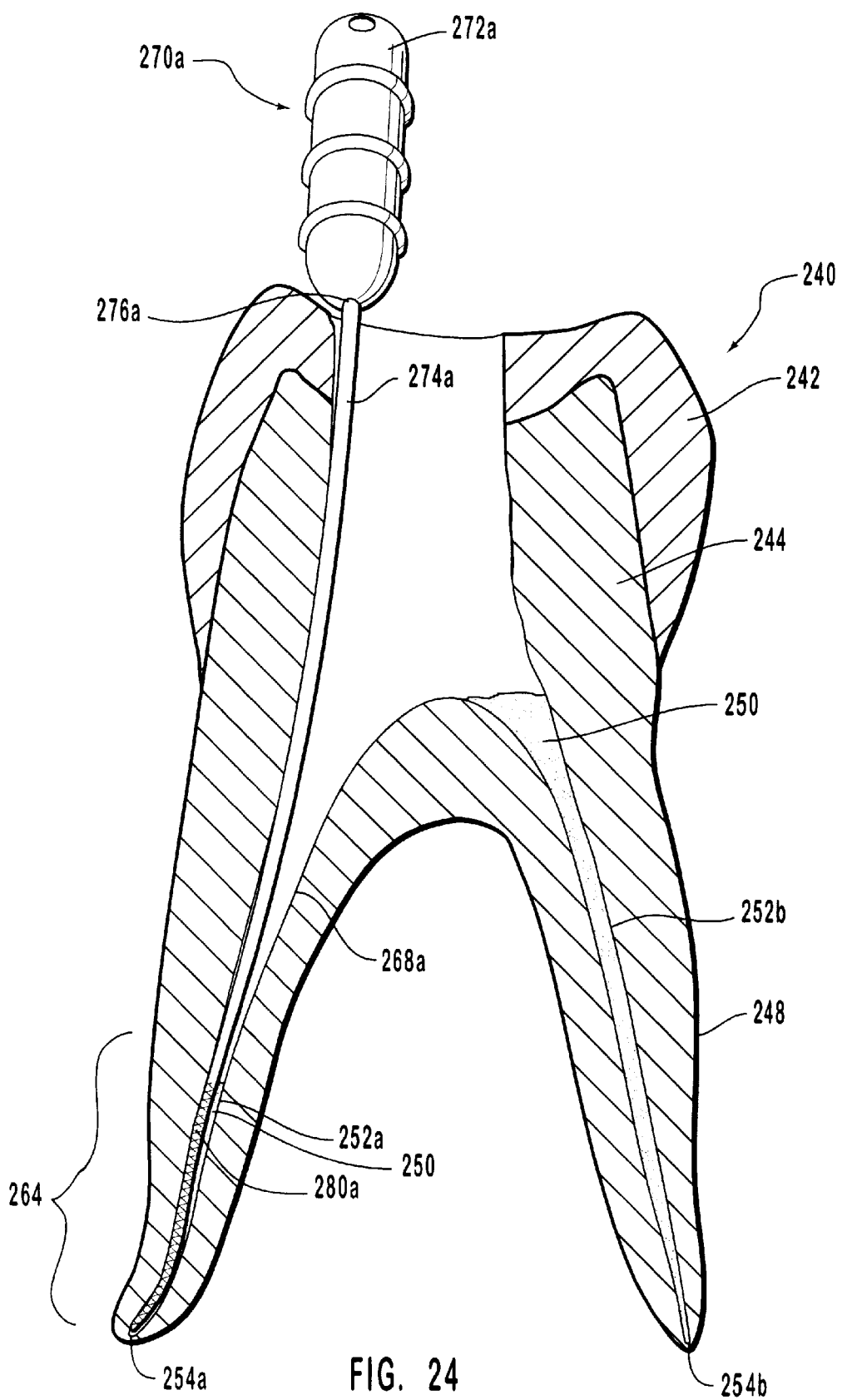
FIG. 24 is a longitudinal cross-sectional view of a tooth with a file inserted into a root canal having a length that is sufficient to reach the apex.

FIG. 24 depicts file 274a inserted into apical portion 264 of root canal 252a. The apical root portion file instruments are generally moved in a different pattern compared to the operative middle portion file instruments due primarily to the different perimeter anatomies of the two portions. A root canal generally becomes more cylindrical towards the apical portion such that a root canal that has a perimeter anatomy that is essentially elliptical in shape within the operative middle portion tapers to an essentially cylindrically shaped perimeter anatomy within the apical portion.

An elliptical perimeter anatomy typically requires that the practioner move the file around the perimeter and/or flex the rotating file against the surfaces or walls in a milling motion such that the tip is moved to many locations around the perimeter. Due to the more cylindrical anatomy of an apical root portion, it becomes much less necessary to flex a rotating file in a milling motion. It is generally adequate to merely rotate the file within the apical root portion and/or move the file in a longitudinal motion. More specifically, after the file reaches the apex or approximately reaches the apex, the file is preferably moved upward while simultaneously being rotated.

Since file 274a is generally not moved around the perimeter as in cleaning the operative middle portion, the center of motion, such as the center of rotation, of file 274a generally corresponds with the center of the root canal. In contrast, the center of motion when the operative middle portion is cleaned is at various locations as the file is moved around the root canal.

The files used to clean the apical root portion can be designed for primarily longitudinal movement, rotational movement or combinations thereof. However, since it is generally not necessary to flex a file when cleaning the apical root portion, apical root portion files need not necessarily have the same properties as the operative middle portion files in terms of flexibility, rigidity and resilience. The files of the apical portion file instruments are however preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion even after the file has moved throughout the length of the root canal. Additionally, a file of an apical root portion file instrument preferably has adequate resilience to avoid being substantially deformed as the file passes through a root canal and also as the abrading portion is urged against the walls of the root canal.

FIG. 25A depicts a longitudinal cross-sectional view of tooth 240 after both root canals 252a and 252b have been cleaned. FIG. 25B depicts a cross-sectional view of tooth 240 taken along cutting line 25B—25B in FIG. 25A. From the view shown in FIG. 25B, it is clear that essentially all pulp material 250 has been removed from root canal 252a. FIG. 25C is a transverse cross-sectional view of root canal 252a taken along cutting line 25C—25C in FIG. 25A through cementum 248 and dentin 244 to depict the configuration of the cleaned and shaped root canal. The view shown in FIG. 25C shows in phantom lines the original configuration of the perimeter of the pulp canal 252a and the configuration of the cleaned and shaped walls 268a.

While the root canal is cleaned, it is also generally simultaneously shaped for subsequent filling with a filling material such as gutta percha. Cleaning and shaping a root canal, such as pulp canal 252a, to yield a cleaned and shaped root canal, such as shaped walls 268a, generally necessitates the widening of portions of the pulp canal and smoothing some contours of the pulp canal to yield a wider and smoother canal. The amount of dentin removed during the cleaning and shaping is preferably no more than just sufficient to adequately shape the root canal for subsequent filling.

Figure 1A:
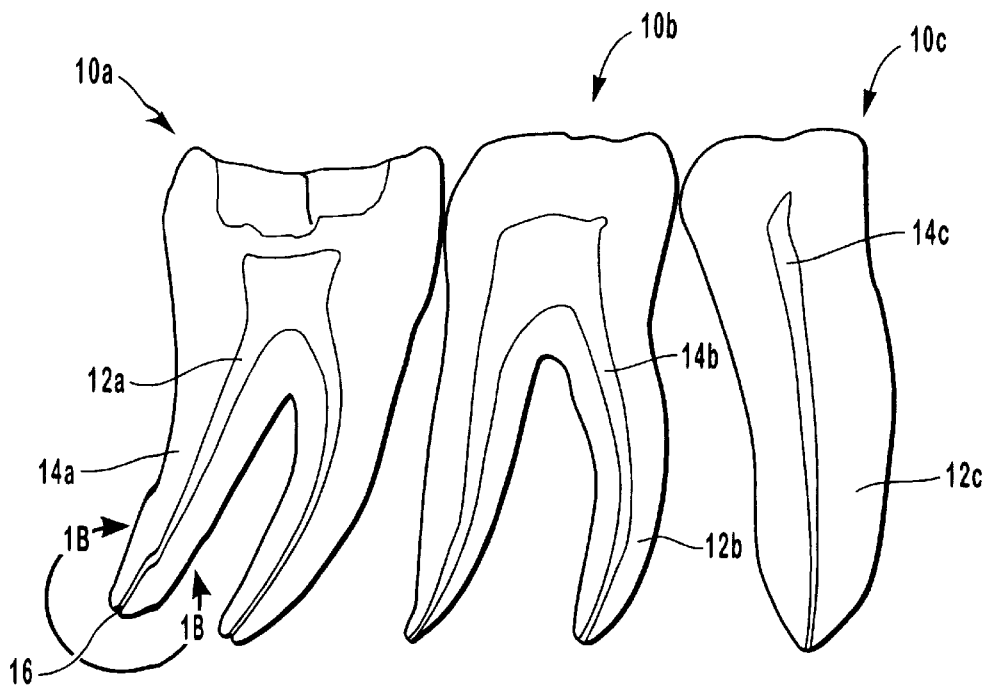
FIG. 1A is a perspective view of an x-ray image of several adjacent teeth taken in vivo.
Figure 1B:
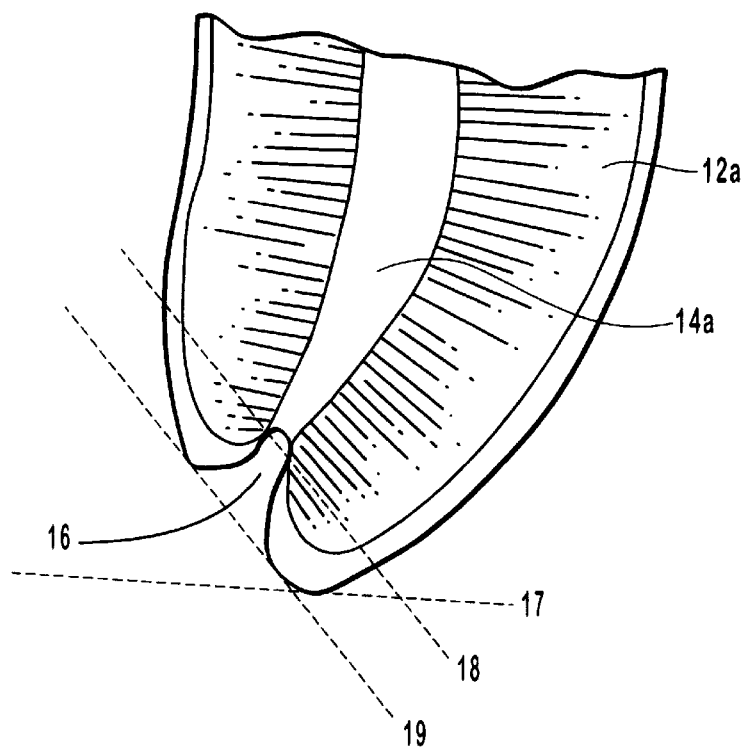
FIG. 1B is an enlarged perspective view of a root of a tooth shown in FIG. 1A.
Figure 2:
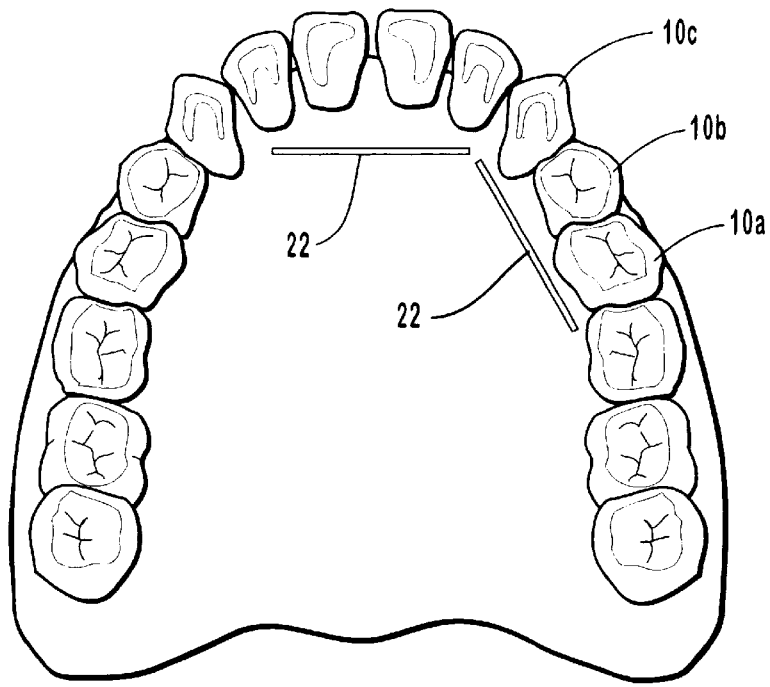
FIG. 2 is a perspective view of a x-ray film positioned adjacent to teeth to produce an image as shown in FIG. 1A.
Figures 3A, 3B:
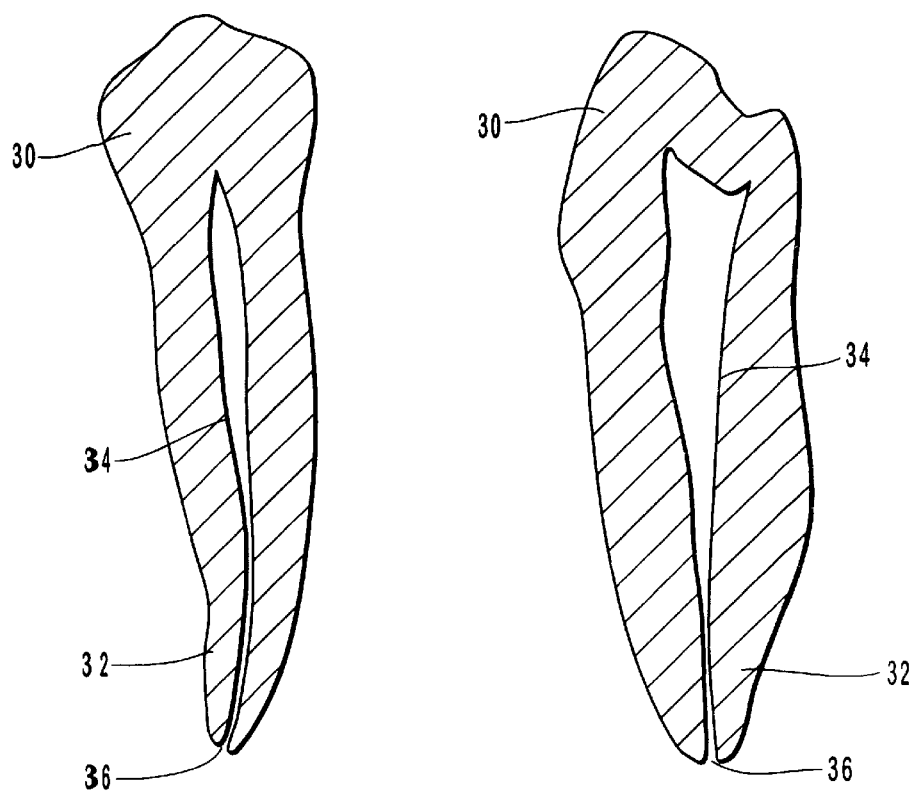
FIG. 3A is a longitudinal cross-sectional view of an extracted lower premolar to show the anatomy of the tooth from the buccal-lingual view.
FIG. 3B is a longitudinal cross-sectional view of the extracted lower premolar shown in FIG. 3A from the mesial-distal view.
Figure 6A:
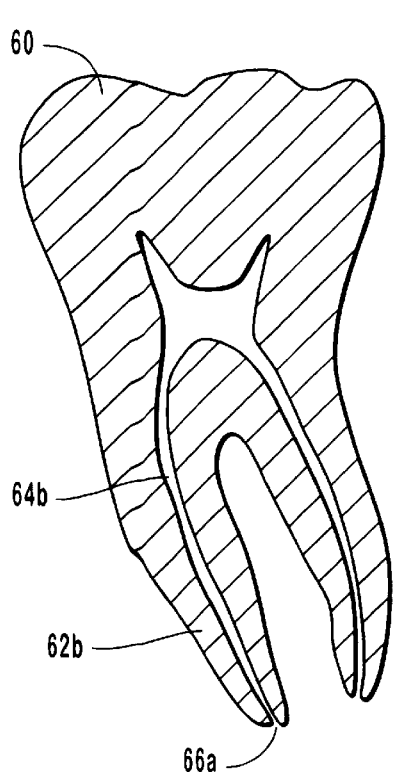
FIG. 6A is a longitudinal cross-sectional view of an extracted lower first molar to show the anatomy of the tooth from the buccal-lingual view.
Figure 6B:
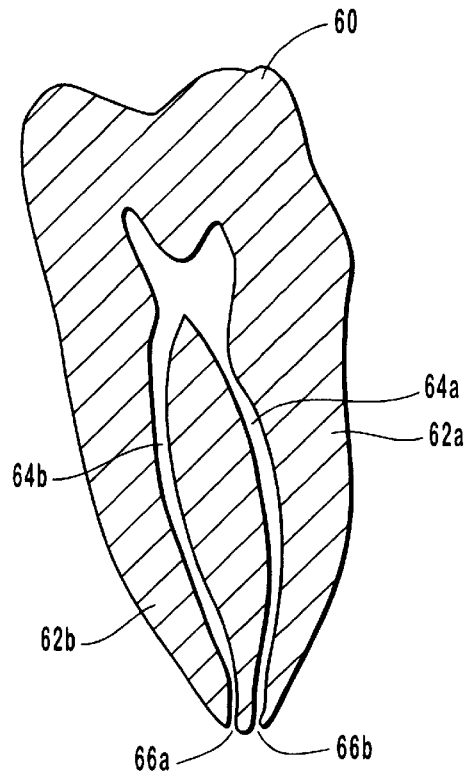
FIG. 6B is a longitudinal cross-sectional view of the extracted lower first molar shown in FIG. 6A from the mesial-distal view.
Figure 7A:
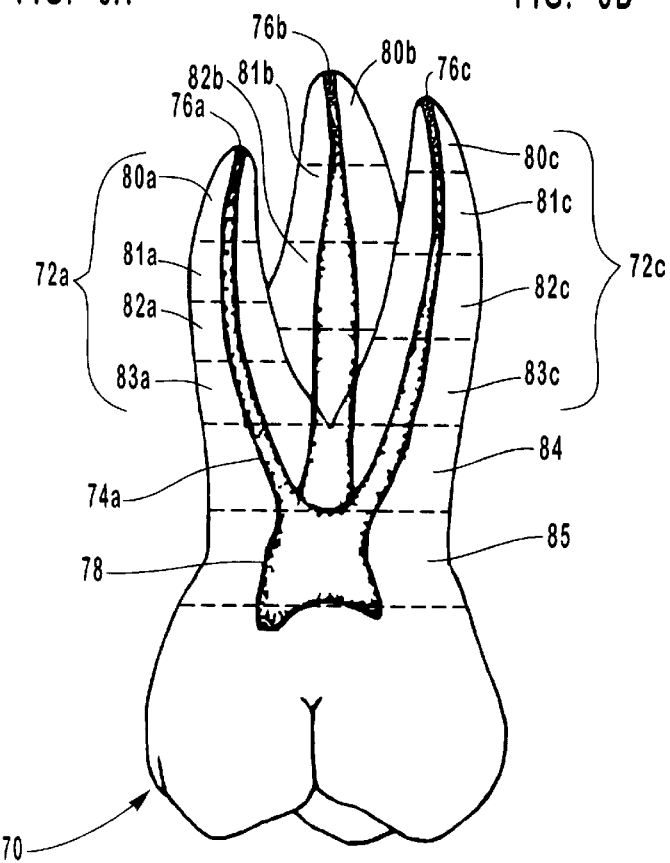
FIG. 7A is a schematic perspective view of an extracted maxillary right first molar with cutting lines which show the division of the tooth into transverse cross-sectional segments.
Figure 7B:
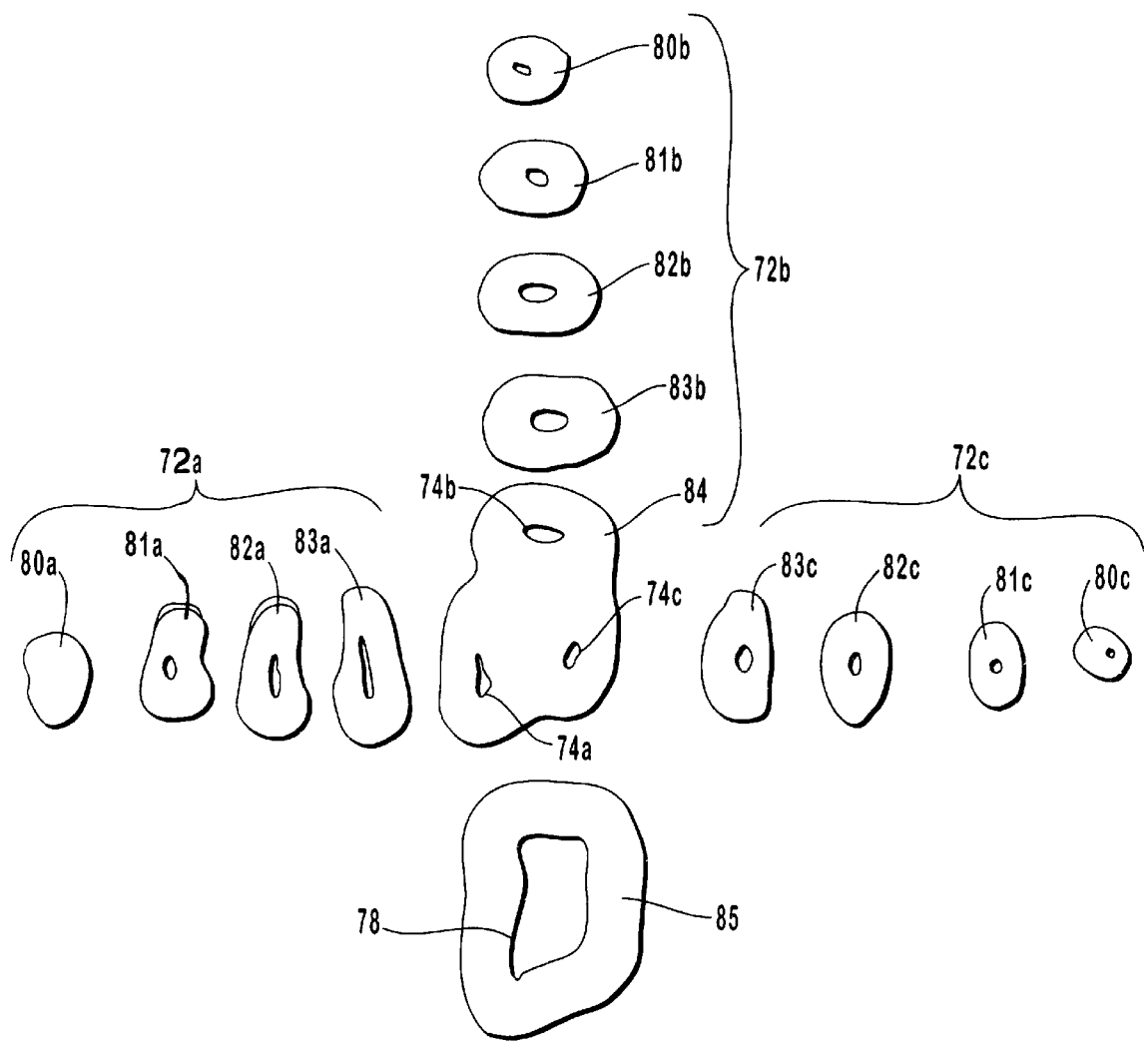
FIG. 7B is shows the segments of the molar shown in FIG. 7B to clearly show the variations of the root canals.
Figure 8:
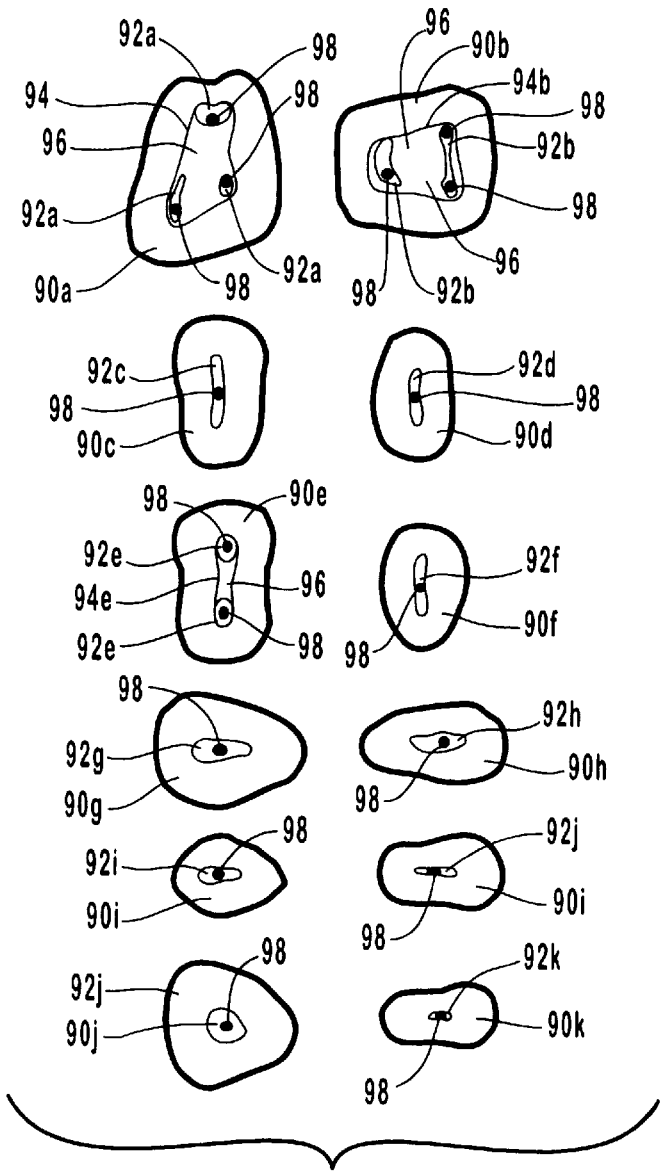
FIG. 8 is a cross-sectional view of extracted teeth which have been cut along into transverse cross-sectional segments to show the anatomy of various root canals.
Figure 9:
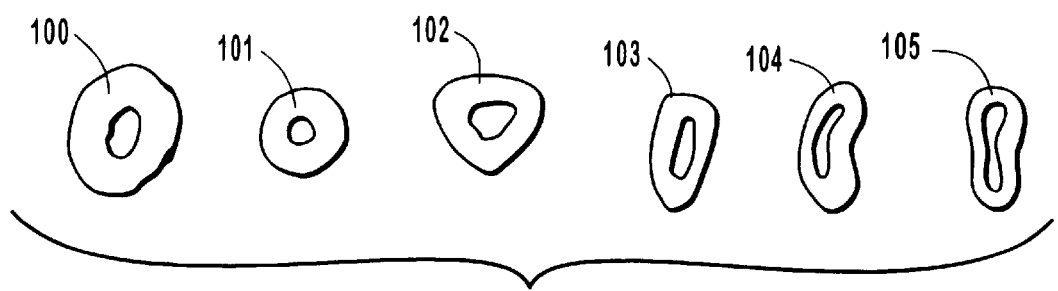
FIG. 9 is a cross-sectional view of extracted teeth which have been cut along into transverse cross-sectional segments to show the general categorization of root canal perimetrical anatomies.
Figure 10A:
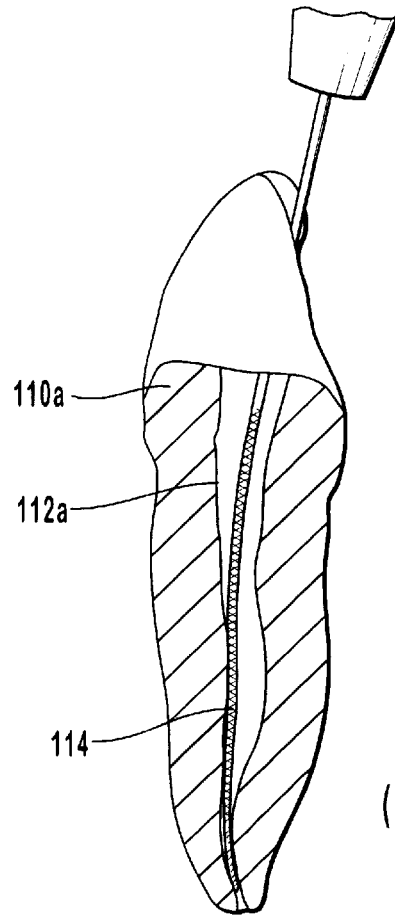
FIG. 10A is a perspective view of a prior art instrument cleaning a tooth that has been partially cut-away to reveal the inability of the instrument to clean the root canal.
Figure 10B:
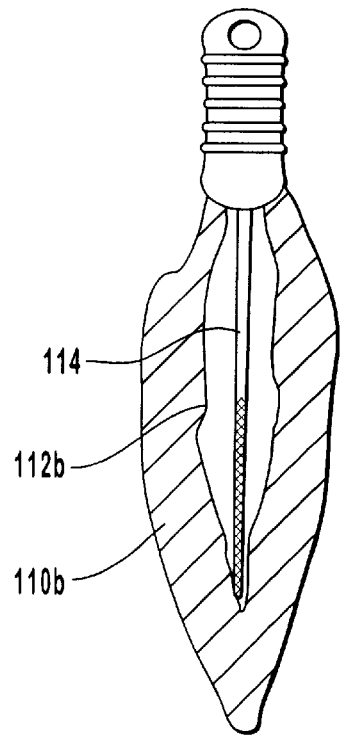
FIG. 10B is a perspective view of a prior art instrument cleaning another tooth that has been partially cut-away to reveal the inability of the instrument to clean the root canal.

Because the perimeter of the root canal is followed during cleaning and shaping of the root canal, the original anatomy of the root canal or shape of the perimeter is substantially maintained. According, when the original perimeter is, for example, generally elliptical such as the cross-sectional shape of pulp canal 252a, the resulting cleaned and shaped root canal has a perimeter that is still generally elliptical such as shaped walls 268a as shown in FIG. 25C. Similarly, if the original shape of the perimeter of a root canal as seen from a transverse cross-sectional view, such as the anatomies or perimeter configurations shown in FIGS. 7B, 8 and 9, is generally circular, laminar or tear shaped, then the cleaned and shaped walls will also be generally circular or tear shaped. In other words, the original anatomy of the root-canal controls the shape of the resulting cleaned and shaped anatomy due to the cleaning techniques enabled by the present invention.

In contrast, prior art methods yield a final anatomy that is dictated by the shape of the instrument. As shown in FIGS. 15A–F, prior art methods result in an anatomy with a significant footprint from the instrument without even cleaning all of the perimeter of the root canal. In addition to failing to fully clean the root canal, the tooth can be overly thinned, perforations may result or the tooth may be unnecessarily weakened when cleaned by such prior art methods.

FIGS. 26A–26J are transverse cross-sections of exemplary files that can be utilized to clean the operative middle portion or the apical root portion of the root canal. Each file has a different abrading portion. All of the files in combination with their respective abrading portions disclosed herein are examples of means for removal and cleaning of pulp material as the file instrument is operatively moved. Additionally, each abrading portion disclosed herein is an example of a means for abrading a root canal.

Conventional file designs can also be utilized within the scope of the present invention. Accordingly, the files are not limited to the designs shown in FIGS. 26A–26J. The files preferably, however, are configured in a manner such that when the potential for breakage is minimized. For example, a file with a square cross-section may be preferred over a triangular cross-section as the file with a square cross-section has a greater mass and is accordingly less likely to break. Additionally, a file configured with tines or extensions having wide angles are generally preferred over those with narrow angles. However, the preferred tine configuration depends primarily on the particular use as in some instances it is desirable to aggressively cut while in others the root can be passively cut. When it is more desirable to aggressively cut, it may be preferred for example to utilize a file with relatively narrow tines.

FIG. 26 depicts a file 310 with a generally square-shaped transverse cross-section and truncated corners 312. Abrasive grit 314 is located on truncated corners 312. Similarly such abrasive grit can be located around a file with any cross-sections and be an effective abrading portion.

Figure 26A:
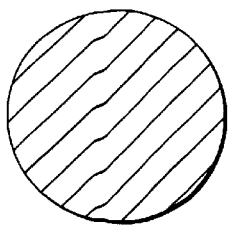
FIGS. 26A–J are transverse cross-sectional views of endodontic files.
Figure 26B:
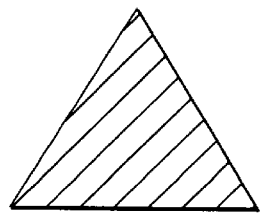
Figure 26C:
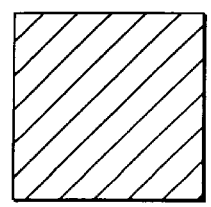
Figure 26D:
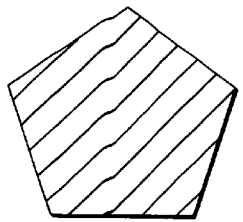
Figure 26E:
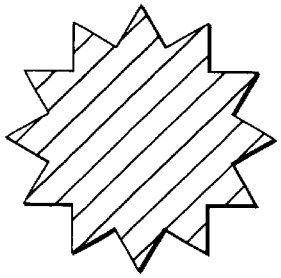
Figure 26F:
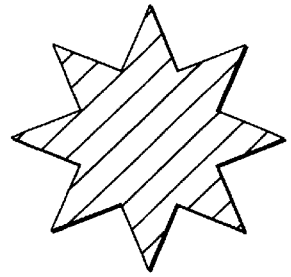
Figure 26G:
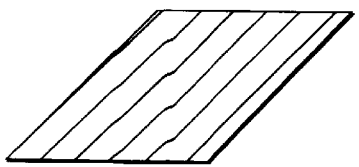
Figure 26H:
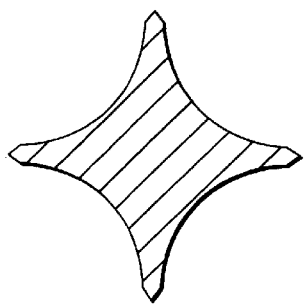
Figure 26I:
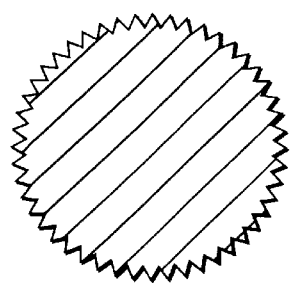
Figure 26J:
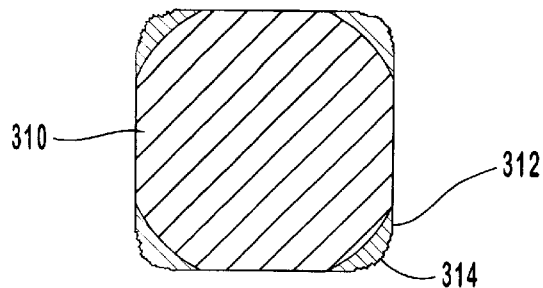
Figure 27:
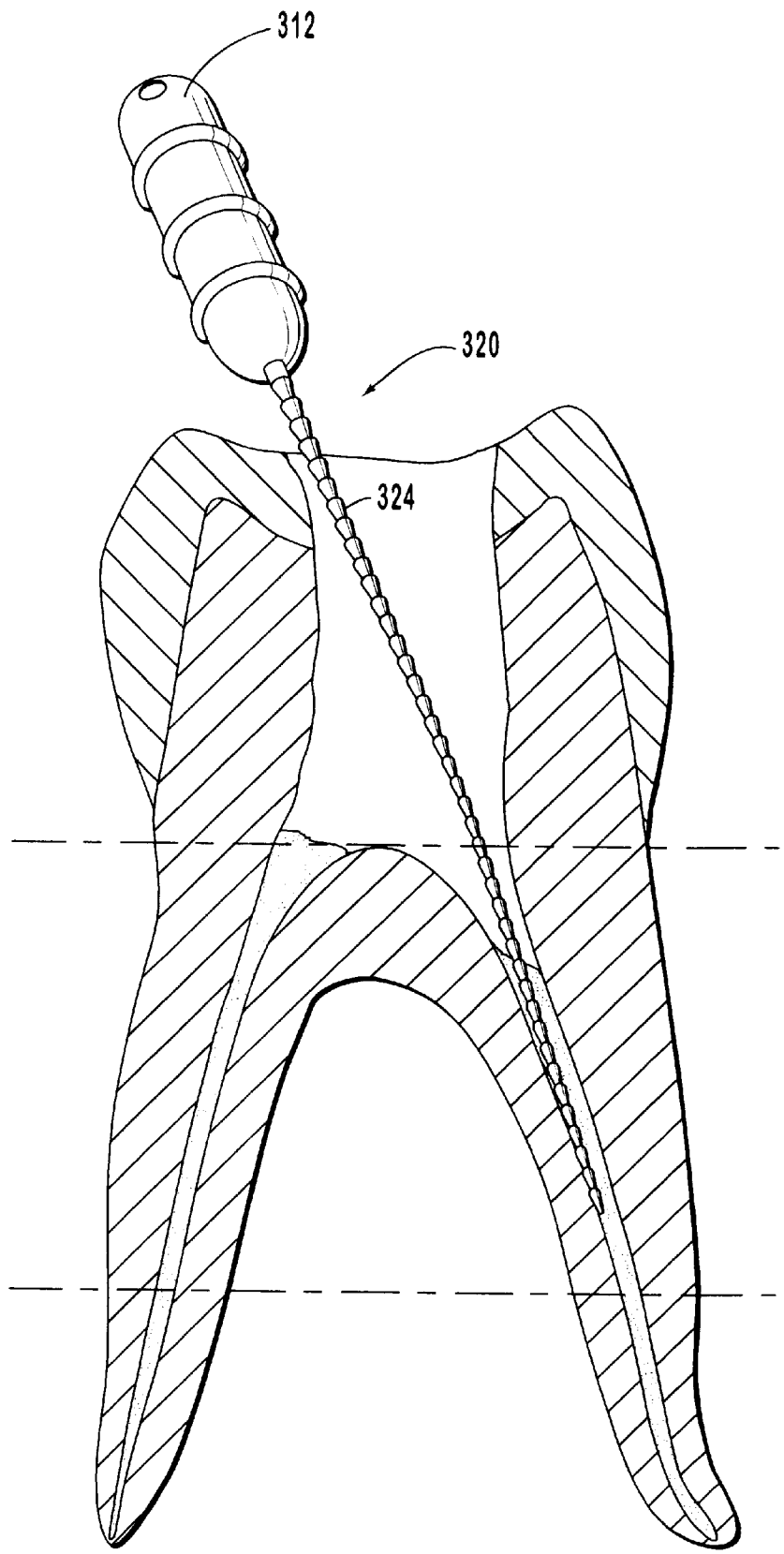
FIG. 27 is a longitudinal cross-sectional view of a tooth with a root canal being cleaned with a file instrument having a file formed by machining a groove into a metal blank.

The transverse cross-section of a file shown at FIG. 26A corresponds to a file as shown in FIG. 17A. In FIG. 27, a file instrument 320 is shown cleaning operative middle portion 160 of a root canal. File instrument 320 has a handle 322 connected to file 324 formed by machining a groove into a metal blank.

Figure 28:
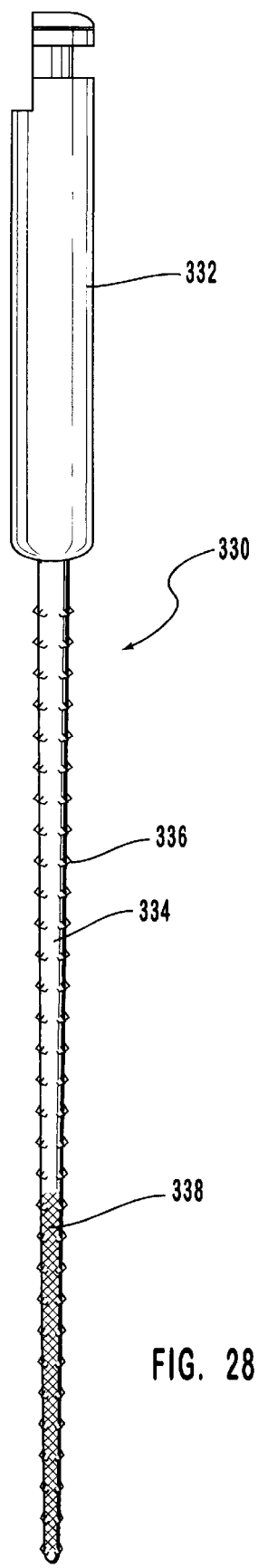
FIG. 28 is a perspective view of another embodiment of an endodontic instrument.
Figure 29:
FIG. 29 is a partial perspective view of an endodontic file depicting the tip of the file.
Figure 30:
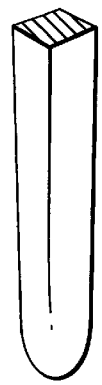
FIG. 30 is a partial perspective view of an endodontic file depicting the tip of the file.
Figure 31:
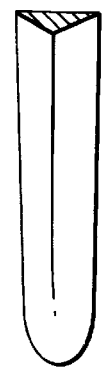
FIG. 31 is a partial perspective view of an endodontic file depicting the tip of the file.
Figure 32:
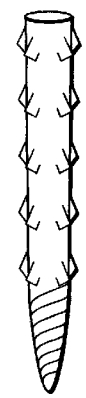
FIG. 32 is a partial perspective view of an endodontic file depicting the tip of the file.

FIG. 28 depicts another embodiment of a file instrument shown at 330. File instrument 330 has a handle 332 which is particularly adapted for use with a mechanical instrument. The file instruments of the present invention can, however, be utilized with any suitable handle configuration. All of the handles disclosed herein are examples of end means for grasping and operatively moving a file in an abrasive action.

File instrument 330 further comprises a file 334 which is preferably used to clean the operative middle portion. File 334 has an abrading portion comprising barbs 336 at the upper end of the file and a combination of tines 336 and knurled surface 338 at the lower end. FIGS. 29–32 are depictions of various tips of files within the scope of the present invention.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An endodontic instrument system adapted for anatomical removal and for anatomical cleaning of essentially all pulp material from the operative middle portion and the apical root portion of an operative root canal in a tooth, the endodontic instrument system comprising:

a first endodontic instrument means for anatomical removal and anatomical cleaning of essentially all pulp material from the operative middle portion without significantly extending into the apical root portion, said first endodontic instrument means comprising:

operative middle portion instrument means for flexibly conforming to the anatomical shape of the operative middle portion so as to effect removal and cleaning of pulp material as the first instrument means is operatively moved, said operative middle portion instrument means having an abrading portion with a length corresponding to at least the length of the operative middle portion in order to remove pulp material from essentially all of the operative middle portion of the root canal, said operative middle portion instrument means being able to flex such that the abrading portion is urged against root canal surfaces while the operative middle portion instrument means is rotated and moved in a cleaning motion, thereby enabling contours of the operative middle portion to be used as a guide for movement of the operative middle portion instrument means in order to conform to the anatomical shape of the operative middle portion; and end means for grasping and operatively moving in an abrasive action the operative middle portion instrument means while bending and flexing the operative middle portion instrument means; and a second endodontic instrument means for removal and cleaning of essentially all remaining pulp material from the apical root portion after the pulp material has been essentially removed from the operative middle portion.

2. An endodontic instrument system as defined in claim 1, wherein the operative middle portion instrument means has sufficient rigidity to apply pressure against the root canal surfaces via the abrading portion as the operative middle portion instrument means is flexed or curved to urge the abrading portion against root canal surfaces and simultaneously moved in a cleaning motion.

3. An endodontic instrument system as defined in claim 1, wherein the operative middle portion instrument means has adequate resilience to avoid being substantially deformed as the operative middle portion instrument means is flexed or curved to urge the abrading portion against root canal surfaces and as the operative middle portion instrument means is simultaneously moved in a cleaning motion.

4. An endodontic instrument system as defined in claim 1, wherein the operative middle portion instrument means is configured to enable a practitioner to move the operative middle portion instrument means around the perimeter of the operative middle portion of the root canal.

5. An endodontic instrument system as defined in claim 1, wherein the operative middle portion instrument means is a file having a tip and wherein the file is configured to enable a practitioner to move the file along a side of the operative middle portion in a manner such that the tip does not remain primarily in one position as the operative middle portion is cleaned.

6. An endodontic instrument system as defined in claim 1, wherein the first endodontic instrument means comprises a set of instruments.

7. An endodontic instrument system as defined in claim 1, wherein the operative middle portion instrument means comprises a file.

8. An endodontic instrument system as defined in claim 1, wherein the operative middle portion instrument means comprises a file having a length within a range from about 8 mm to about 35 mm.

9. An endodontic instrument system as defined in claim 1, wherein the operative middle portion instrument means comprises a file having a tip opposite a top end that is connected to the end means, and wherein the tip has a diameter in a range from about 0.06 mm to about 0.4 mm.

10. An endodontic instrument system as defined in claim 1, wherein the operative middle portion instrument means comprises a file having a tip opposite a top end that is connected to the end means, and wherein the top end has a diameter in a range from about 0.25 mm to about 2 mm.

11. An endodontic instrument system as defined in claim 1, wherein the operative middle portion instrument means comprises a set of instruments, wherein each instrument has essentially the same length.

12. An endodontic instrument system as defined in claim 1, wherein the operative middle portion instrument means comprises a set of instruments, wherein each operative middle portion instrument comprises a file having a tip opposite a top end, wherein the files of all of the instruments in the set have essentially the same tip diameter while having distinct top end diameters to enable the files to be sequentially introduced into the operative middle portion such that each successive file has a greater top end diameter than that of the preceding file.

13. An endodontic instrument system as defined in claim 1, wherein the operative middle portion instrument means comprises a set of instruments, wherein each operative middle portion instrument comprises a file, wherein the files of all of the instruments in the set have distinct tapers to enable the files to be sequentially introduced into the operative middle portion such that each successive file has a greater taper than that of the preceding file.

14. An endodontic instrument system as defined in claim 1, wherein the operative middle portion instrument means comprises a file having a tip opposite a top end, wherein the tip is configured for at least minimal cutting capability.

15. An endodontic instrument system as defined in claim 1, wherein the operative middle portion instrument means comprises a file having a tip opposite a top end, wherein the tip is configured for essentially no cutting capability.

16. An endodontic instrument system as defined in claim 1, wherein the abrading portion of the operative middle portion instrument means is sufficiently long to enable the abrading portion to also abrade surfaces above the operative middle portion of the operative root canal during cleaning of the operative middle portion.

17. An endodontic instrument system as defined in claim 1, wherein the second endodontic instrument means comprises a file with a top end extending from end means for grasping and operatively moving the file, wherein the file has a tip opposite the top end, wherein the file further comprises an abrading means extending from the tip along at least a portion of the file.

18. An endodontic instrument system as defined in claim 1, wherein the second endodontic instrument means comprises a file with a top end extending from end means for grasping and operatively moving the file, wherein the file has a rounded tip opposite the top end, wherein the file further comprises an abrading means extending from the tip along at least a portion of the file.

19. An endodontic instrument system as defined in claim 1, wherein the end means is configured for positioning on the occlusal surface of a tooth to serve as a stop.

20. An endodontic instrument system adapted for anatomical removal and for anatomical cleaning of essentially all pulp material from the operative middle portion and the apical root portion of an operative root canal in a tooth, the endodontic instrument system comprising:

a first endodontic instrument configured for use in the operative middle portion of an operative root canal to anatomically clean essentially all pulp material from the operative middle portion without significantly extending into the apical root portion, comprising
a file having a top end opposite a tip, the file having a length that limits the penetration of the tip of the file in the operative root canal to essentially only the operative middle portion of the operative root canal, the file having an abrading means for removing pulp material, the abrading means being located on the file and having a length corresponding to at least the length of the operative middle portion, the file being characterized in that the file is able to flex such that the abrading means is urged against root canal surfaces while the file is rotated and moved in a cleaning motion, thereby enabling contours of the operative middle portion to be used as a guide for movement of the file in order to conform to the anatomical shape of the operative middle portion while effecting removal and cleaning of pulp material from essentially all of the operative middle portion; and
end means for grasping and operatively moving the file in an abrasive action while bending and flexing the file within the operative middle portion, wherein the end means is connected to the top end of the file of the first endodontic instrument; and a second endodontic instrument configured for removal and cleaning of essentially all remaining pulp material from the root portion after the pulp material has been removed from the operative middle portion, the second endodontic instrument comprising
a file having a top end opposite a tip, the file having a length that enables the tip of the file to reach within the apical portion of the root canal, the file having an abrading means for removing pulp material, the abrading means being located on a portion of the file such that the abrading means can remove the pulp material from the apical portion of the root canal; and
end means for grasping and operatively moving the file in an abrasive action within the apical root portion, wherein the end means is connected to the top end of the file of the second endodontic instrument.

21. An endodontic instrument system as defined in claim 20, wherein the file of the first endodontic instrument has sufficient rigidity to apply pressure against the root canal surfaces via the abrading means as the file is flexed or curved to urge the abrading means against root canal surfaces and as the file is simultaneously moved in a cleaning motion.

22. An endodontic instrument system as defined in claim 20, wherein the file of the first endodontic instrument has adequate resilience to avoid being substantially deformed as the file is flexed or curved to urge the abrading means against root canal surfaces and as the file is simultaneously moved in a cleaning motion.

23. An endodontic instrument system as defined in claim 20, wherein the file of the first endodontic instrument is configured to enable a practitioner to move the file around the perimeter of the operative middle portion of the root canal.

24. An endodontic instrument system as defined in claim 20, wherein the file of the first endodontic instrument is configured to enable a practitioner to move the file along a side of the operative middle portion in a manner such that the tip does not remain primarily in one position as the operative middle portion is cleaned.

25. An endodontic instrument system as defined in claim 20, wherein the file of the first endodontic instrument has a length within a range from about 8 mm to about 35 mm.

26. An endodontic instrument system as defined in claim 20, wherein the tip of the file of the first endodontic instrument has a diameter in a range from about 0.06 mm to about 0.4 mm.

27. An endodontic instrument system as defined in claim 20, wherein the top end of the file of the first endodontic instrument has a diameter in a range from about 0.25 mm to about 2 mm.

28. An endodontic instrument system as defined in claim 20, wherein the tip of the file of the first endodontic instrument is configured for at least minimal cutting capability.

29. An endodontic instrument system as defined in claim 20, wherein the tip of the file of the first endodontic instrument is configured for essentially no cutting capability.

30. An endodontic instrument system as defined in claim 20, wherein the abrading means of the file of the first endodontic instrument is sufficiently long to enable the abrading means to also abrade surfaces above the operative middle portion of the operative root canal during cleaning of the operative middle portion.

31. An endodontic instrument system as defined in claim 20, wherein the tip of the file of the second endodontic instrument is rounded.

32. An endodontic instrument system as defined in claim 20, wherein the end means for both the first and the second endodontic instruments is configured for positioning on the occlusal surface of a tooth to serve as a stop.

33. An endodontic instrument system adapted for anatomical removal and for anatomical cleaning of essentially all pulp material from the operative middle portion and the apical root portion of an operative root canal in a tooth, the endodontic instrument system comprising:

a set of first endodontic instruments configured for sequential use in the operative middle portion of an operative root canal to anatomically clean essentially all pulp material from the operative middle portion without significantly extending into the apical root portion, each instrument in the set comprising a file having a tip opposite a top end, the file having a length that limits the penetration of the tip of the file in the root canal to essentially only the operative middle portion of the root canal, the file having an abrading means for removing pulp material, the abrading means being located on the file and extending from the tip along at least most of the file toward the top end, the file being characterized in that the file is able to flex such that the abrading means is urged against root canal surfaces while the file is rotated and moved in a cleaning motion, thereby enabling contours of the operative middle portion to be used as a guide for movement of the file in order to conform to the anatomical shape of the operative middle portion while effecting removal and cleaning of pulp material from essentially all of the operative middle portion; and a handle connected to the top end of the file, the handle being configured to enable a user to grasp and operatively move the file in an abrasive action while bending and flexing the file within the operative middle portion of the root canal; and a set of second endodontic instruments configured for removal and cleaning of essentially all remaining pulp material from the apical root portion after the pulp material has been removed from the operative middle portion, the second endodontic instrument comprising a file having a tip opposite a top end, the file having a length that enables the tip of the file to reach within the apical portion of the root canal, the file having an abrading means for removing pulp material, the abrading means being located on a portion of the file such that the abrading means can remove the pulp material from the apical portion of the root canal; and a handle connected to the top end of the file and being configured to enable a user to grasp and operatively move the file in an abrasive action within the apical root portion of the root canal.

34. An endodontic instrument system as defined in claim 33, wherein the file of each instrument in the set of first endodontic instruments has sufficient rigidity to apply pressure against the root canal surfaces via the abrading means as each file is flexed or curved to urge the abrading means against root canal surfaces and as each file is simultaneously moved in a cleaning motion.

35. An endodontic instrument system as defined in claim 33, wherein the file of each instrument in the set of first endodontic instruments has adequate resilience to avoid being substantially deformed as each file is flexed or curved to urge the abrading means against root canal surfaces and as each file is simultaneously moved in a cleaning motion.

36. An endodontic instrument system as defined in claim 33, wherein the file of each instrument in the set of first endodontic instruments is configured to enable a practitioner to move the file around the perimeter of the operative middle portion of the root canal.

37. An endodontic instrument system as defined in claim 33, wherein the file of each instrument in the set of first endodontic instruments is configured to enable a practitioner to move the file along a side of the operative middle portion in a manner such that the tip does not remain primarily in one position as the operative middle portion is cleaned.

38. An endodontic instrument system as defined in claim 33, wherein the file of each instrument in the set of first endodontic instruments has a length within a range from about 8 mm to about 35 mm.

39. An endodontic instrument system as defined in claim 33, wherein the tip of each file of each instrument in the set of first endodontic instruments has a diameter in a range from about 0.08 mm to about 0.3 mm.

40. An endodontic instrument system as defined in claim 33, wherein the top end of each file of each instrument in the set of first endodontic instruments has a diameter in a range from about 0.25 mm to about 2 mm.

41. An endodontic instrument system as defined in claim 33, wherein the file of each instrument in the set of first endodontic instruments has essentially the same length.

42. An endodontic instrument system as defined in claim 33, wherein the files of all of the instruments in the set of first endodontic instruments have essentially the same tip diameter while having distinct top end diameters to enable the files to be sequentially introduced into the operative middle portion such that each successive file has a greater top end diameter than that of the preceding file.

43. An endodontic instrument system as defined in claim 33, wherein the files of all of the instruments in the set of first endodontic instruments have distinct tapers to enable the files to be sequentially introduced into the operative middle portion such that each successive file has a greater taper than that of the preceding file.

44. An endodontic instrument system as defined in claim 33, wherein the tip of each file in the set of first endodontic instruments is configured for at least minimal cutting capability.

45. An endodontic instrument system as defined in claim 33, wherein the tip of each file in the set of first endodontic instruments is configured for essentially no cutting capability.

46. An endodontic instrument system as defined in claim 33, wherein the abrading means of each file in the set of first endodontic instrument is sufficiently long to enable the abrading means of each file to also abrade surfaces above the operative middle portion of the operative root canal during cleaning of the operative middle portion.

47. An endodontic instrument system as defined in claim 33, wherein the tip of each file in the set of second endodontic instruments is rounded.

48. An endodontic instrument system as defined in claim 33, wherein the handle of each instrument in the set of first endodontic instruments and the handle of each instrument in the set of second endodontic instruments is configured for positioning on the occlusal surface of a tooth to serve as a stop.

49. An endodontic instrument system adapted for anatomical removal and for anatomical cleaning of essentially all pulp material from the operative middle portion and the apical root portion of an operative root canal in a tooth, the endodontic instrument system comprising a set of first endodontic instruments configured for sequential use in the operative middle portion of a tooth to anatomically clean essentially all pulp material from the operative middle portion without significantly extending into the apical root portion, each instrument in the set comprising a file having a tip opposite a top end, the file having a length that limits the penetration of the tip of the file in the root canal to essentially only the operative middle portion of the root canal, the file having an abrading means for removing pulp material, the abrading means being located on the file and extending from the tip along at least most of the file toward the top end, the file being characterized in that the file is able to flex such that the abrading means is urged against root canal surfaces while the file is rotated and moved in a cleaning motion, thereby enabling contours of the operative middle portion to be used as a guide for movement of the file in order to conform to the anatomical shape of the operative middle portion while effecting removal and cleaning of pulp material from essentially all of the operative middle portion; and a handle connected to the top end of the file such that movement of the handle also moves the file, the handle being configured to enable a user to grasp and operatively move the file in an abrasive action while bending and flexing the file within the operative middle portion of the root canal; and wherein the files of all of the instruments in the set of first endodontic instruments have essentially the same length and tip diameter while having distinct top end diameters to enable files to be sequentially introduced into the operative middle portion such that each successive file has a greater top end diameter than that of the preceding file; and a set of second endodontic instruments configured for removal and cleaning of essentially all remaining pulp material from the apical root portion after the pulp material has been removed from the operative middle portion, the second endodontic instrument comprising a file having a tip opposite a top end, the file having a length that enables the tip of the file to reach within the apical portion of the root canal, the file having an abrading means for removing pulp material, the abrading means being located on a portion of the file such that the abrading means can remove the pulp material from the apical portion of the root canal; and a handle connected to the top end of the file and being configured to enable a user to grasp and operatively move the file in an abrasive action within the apical root portion of the root canal.

* * * * *

UNITED STATES PATENT AND TRADEMARK OFFICE
CERTIFICATE OF CORRECTION

PATENT NO.   : 6,042,375
DATED        : March 28, 2000
INVENTOR(S)  : Francesco Riitano It is certified that error appears in the above-identified patent and that said Letters Patent are hereby corrected as shown below:

Col. 1, ln. 51: after " of the" delete [the]

Col. 1, ln. 52: after "use in" and before "root" insert --the--

Col. 2, ln. 49: after "accurately" change "ascertains" to --ascertain--

Col. 4, ln. 39: after "opposite" change "atop" to --a top--

Col. 5, ln. 13: after "and as" and before "result" insert --a--

Figure 15A:
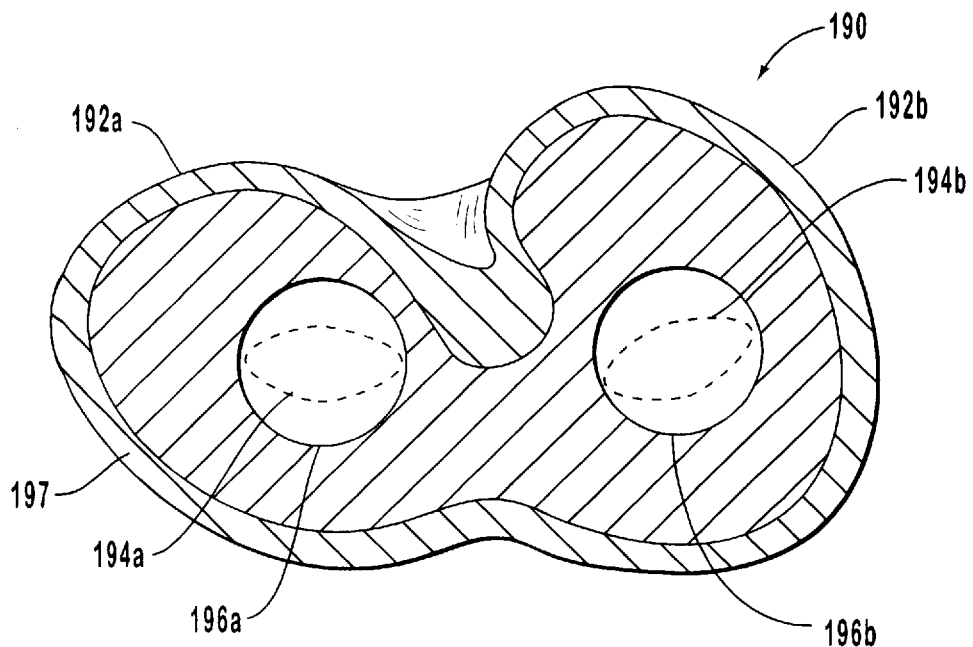
FIG. 15A is a transverse cross-sectional view of a tooth depicting a root canal cleaned by a prior art technique that has resulted in over thinning of the root canal.
Figure 15B:
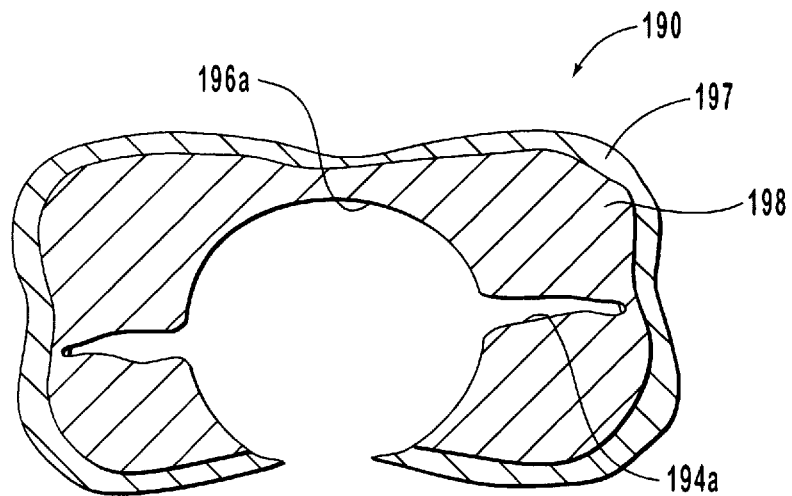
FIG. 15B is a transverse cross-sectional view of a tooth depicting a root canal cleaned by a prior art technique that has resulted in lateral perforation.
Figure 15C:
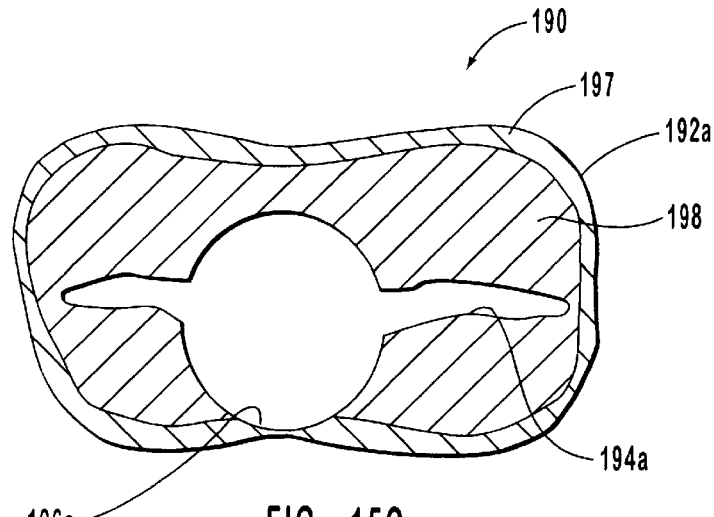
FIG. 15C is a transverse cross-sectional view of a tooth depicting a root canal cleaned by a prior art technique that has resulted in over thinning of the root canal.
Figure 15D:
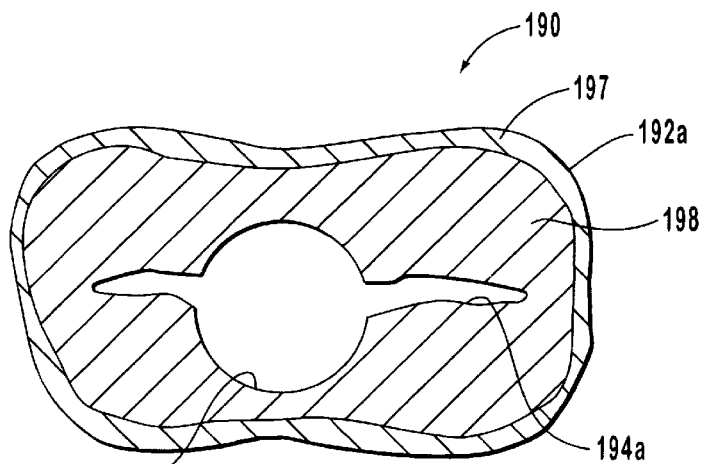
FIG. 15D is a transverse cross-sectional view of a tooth depicting a root canal cleaned by a prior art technique that has resulted in over thinning of the root canal.
Figure 15E:
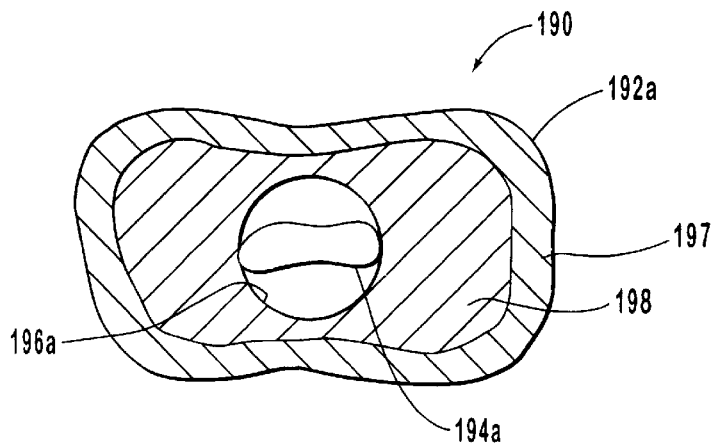
FIG. 15E is a transverse cross-sectional view of a tooth depicting a root canal cleaned by a prior art technique that has resulted in over thinning of the root canal.

Col. 7, ln. 19: after "194a." delete [As in FIG. 15B, the] and insert --The lateral perforation--

Col. 7, ln. 26: after "194a." insert --As in FIG. 15B, the--

Col. 11, ln. 8: after "7B" and before "shows" delete [is]

Col. 11, ln. before "to clearly" change "7B" to --7A--

Col. 15, ln. 1: after "instruments to" and before "used" insert --be--

Col. 22, ln. 11: after "maintained." change "According" to --Accordingly--

UNITED STATES PATENT AND TRADEMARK OFFICE
CERTIFICATE OF CORRECTION

PATENT NO. : 6,042,375
DATED : March 28, 2000
INVENTOR(S) : Francesco Riitano

Page 2 of 2

It is certified that error appears in the above-indentified patent and that said Letters Patent is hereby corrected as shown below:

Col. 23, ln. 18: after "only as" change "illustrated" to --illustrative--

Col. 25, ln. 62: after "from the" and before "root" insert --apical--

Signed and Sealed this

Third Day of April, 2001

*Attest:*

NICHOLAS P. GODICI

*Attesting Officer*     *Acting Director of the United States Patent and Trademark Office*